(12) United States Patent
Lee

(10) Patent No.: US 6,546,786 B2
(45) Date of Patent: Apr. 15, 2003

(54) METHODS AND APPARATUS FOR DETECTION OF RADIOACTIVITY IN LIQUID SAMPLES

(76) Inventor: Dian Y. Lee, 120 Peoples Way, Hockessin, DE (US) 19707

( * ) Notice: Subject to any disclaimer, the term of this patent is extended or adjusted under 35 U.S.C. 154(b) by 0 days.

(21) Appl. No.: 09/820,134

(22) Filed: Mar. 28, 2001

(65) Prior Publication Data

US 2002/0029619 A1 Mar. 14, 2002

Related U.S. Application Data

(60) Provisional application No. 60/221,158, filed on Jul. 27, 2000, and provisional application No. 60/279,264, filed on Mar. 27, 2001.

(51) Int. Cl.$^7$ .............................. G01N 30/00; G01T 1/00
(52) U.S. Cl. ...................................... 73/61.52; 250/328
(58) Field of Search ........................ 73/61.52; 250/328, 250/484.4; 95/87

(56) References Cited

U.S. PATENT DOCUMENTS

| | | | |
|---|---|---|---|
| 4,137,451 A | | 1/1979 | Einolf, Jr. ............. 250/231 SE |
| 4,267,451 A | | 5/1981 | Berick ........................ 250/328 |
| 4,704,531 A | | 11/1987 | Berthold et al. ............ 250/328 |
| 4,956,559 A | * | 9/1990 | Shiraishi .................. 250/484.4 |
| 5,099,129 A | | 3/1992 | Pullan ..................... 250/385.1 |
| 5,166,526 A | | 11/1992 | Dietzel ....................... 250/430 |
| 5,242,471 A | * | 9/1993 | Markham et al. ............... 95/87 |
| 5,283,036 A | | 2/1994 | Hofmann et al. ............. 422/70 |
| 5,559,324 A | | 9/1996 | Rapkin et al. ........... 250/252.1 |
| 5,591,644 A | | 1/1997 | Karmen ....................... 436/53 |
| 6,229,146 B1 | * | 5/2001 | Cochran et al. ............ 250/364 |

FOREIGN PATENT DOCUMENTS

| | | |
|---|---|---|
| WO | WO 99/17104 | 4/1999 |

OTHER PUBLICATIONS

Chapput, A., et al., "Coupling of an analytical liquid chromatograph and a raman spectrometer," 1979, *C.R. Acad. Sc., Ser. C, 289*(11), 293–296 (English abstract).

Fee, D.C., et al., "Multicolumn radio–gas chromatographic analysis of recoil tritium reaction products," *Analytical chemistry*, 1973, 45(11), 1827–1831.

Slavin, W., et al., "A fluorescence detector for high pressure liquid chromatography," *UV Spectrom, Group Bull.*, 1977, 5, 21–37.

* cited by examiner

*Primary Examiner*—Hezron Williams
*Assistant Examiner*—Jay L Politzer
(74) *Attorney, Agent, or Firm*—Michael P. Straher

(57) ABSTRACT

Methods and devices for stop flow detection and measurement of radioactivity in liquid samples are provided. In some embodiments, the invention includes precise positioning of fractions within a flow cell detection area. Novel flow cells and methods providing for flushing samples with gas are also provided.

82 Claims, 8 Drawing Sheets

Precise Positioning of Each Fraction

Before the peak1 coming to the detector

Push-In phase: Precise Positioning of a Fraction

Flushing phase: Flush flow cell to remove memory effect with a Gas (this case, Push-In phase, Fig. 3 can be eliminated) or the agent (cocktail or solvent)

METHODS AND APPARATUS FOR DETECTION OF RADIOACTIVITY IN LIQUID SAMPLES

CROSS REFERENCE TO RELATED APPLICATIONS

This application claims benefit of U.S. provisional application, Ser. No. 60/221,158 filed Jul. 27, 2000 and Ser. No. 60/279,264, filed Mar. 27, 2001, the contents of each of which is hereby incorporated herein by reference in its entirety.

FIELD OF THE INVENTION

This invention relates to methods for detecting and measuring radioactivity in liquid samples and devices for detecting and measuring radioactivity in liquid samples. Particularly, the invention relates to methods of detecting and statically counting concentrations of radioisotopes, and devices for detecting and statically counting concentrations of radioisotopes.

BACKGROUND

Radioisotopes are an important tool in many industries and various types of research, including medical research. For example, radioisotopes are used to label developmental compounds to understand their pharmacokinetics and how they are metabolized in animals and humans. In agrochemical research, radioisotopes are sometimes an important tool for complete understanding of the chemical behavior in the environment. Common radioisotopes used in research include $^{14}C$ and $^{3}H$.

High performance liquid chromatography (HPLC) is widely used for detection and quantifying of radioisotope compounds. Radioactivity flow-through detectors are used to detect radioactive components in an HPLC eluate containing radioisotopes and radioisotope-labeled compounds. There is constant need for improved devices and methods for detecting and quantifying radioisotopes and radioisotope-labeled compounds.

Radioactive decay of a radioisotope is a random process following a Poisson distribution where the standard deviation, $\Sigma$, equals the square root of the total number of times a radioactive decay was observed, or counted, during a counting experiment:

$$\Sigma = \sqrt{\text{Total Number of Decays}}$$

This formula is the basis for calculating the practical lower radioactivity detection limit of a sample containing radioisotopes when combined with information about background levels of radiation. The standard deviation, A, of background radiation produced by a reference sample is expressed in the number of times a radiative decays is measured in the reference sample, i.e. disintegrations per min, "DPM." The scope of radioactivity detection is then expressed using the following equation:

$$Ld \propto \frac{B}{E * T}$$

wherein Ld is the lower limit of detection measured in DPM, B is the background radiation level measured in DPM, E is the counting efficiency measured as a percentage, and T is the length of time spent measuring radioactive decay, i.e. counting time, measured in minutes.

As shown by the formula, the limits of radioactivity detection can be improved by reducing the background level of radioactivity, increasing the counting efficiency of the system, and/or increasing the counting period. Improvement of any one of these parameters would lower the limit of radioactivity detection and thereby enable the measurement of lower concentrations of radioisotopes in a sample.

Several attempts have been made to increase detection sensitivity by reducing background radioactivity levels, increasing counting efficiency, and/or increasing the counting time. For example, Packard Instruments attempted to reduce the background level of radioactivity and thereby lower the limit of radioactivity detection by using time-resolved background reduction technology. Similarly, liquid scintillants can be used to replace solid scintillants for liquid cells in order to increase counting efficiency.

Conventional methods of improving detection sensitivity also involve taking fractions from a continuously running chromatography column and analyzing them in batches, i.e. taking them "off-line," in order to increase counting time. Off-line methods are undesirable because they can not detect and quantitate volatile radioactive components with a very high degree of accuracy because the volatile components tend to evaporate during the fraction collection process.

Conventional methods of increasing counting time are accomplished by collecting eluate in fractions in individual vials using a fraction collector or well fraction collector. Scintillate is then added "off-line" so that the number of radioactive decays can be measured. This manual process is not desirable in modem laboratories because it is labor intensive, inefficient, and costly. An exemplary "off-line" counting process is accomplished by manually collecting fractions in a large number of well plates, such as 96 well plates. The eluate is evaporated and manually counted statically using a multi-well counter.

A stop flow apparatus for determining radioactivity of chromatographic samples is disclosed by Lee, D. Y., PCT/US98/20324 filed Sep. 25, 1998, incorporated herein by reference in its entirety.

Conventional methods have also attempted to lengthen counting time without using a fraction collector. However, these methods fail to accurately detect all radioactive components in samples that contain a number of radioactive components and where the radioactivity of each component is different. Examples of typical methods are provided by A. C. Berick (U.S. Pat. No. 4,137,451. 1981) herein incorporated by reference in its entirety, Berthold (U.S. Pat. No. 4,704,531. 1987) herein incorporated by reference in its entirety, and Dietzel (U.S. Pat. No. 5,166,513. 1992) herein incorporated by reference in its entirety.

A. C. Berick (U.S. Pat. No. 4,137,451. 1981) collects fractions in rotating devices with many tubes that contain scintillant. The tubes are then measured sequentially. Berthold (U.S. Pat. No. 4,704,531. 1987) detects radioactive peaks using a mass detector such as an ultravoilet (UV) detector and then diverts radioisotope containing fractions as they appear as peaks on the UV detector to a radioactivity detector for static counting. In addition, Diezel (U.S. Pat. No. 5,166,513. 1992) detects radioactive peaks using a monitor radioactive detector instead of using a ultraviolet detector, and then diverts radioisotope containing fractions into a secondary radioactivity detector for static counting. In Diezel's attempt, when multiple radioisotope containing fractions elute, the second and subsequent fractions are diverted to a third radioactive detector and subsequent radioactive detectors for static counting. Diezel's method also has the undesirable problem of increased difficulty of recognizing peaks of radioisotope containing fractions on the monitor as radioactivity levels get closer to background levels of radioactivity. Therefore, methods and devices that address these needs have long been sought.

SUMMARY OF THE INVENTION

An apparatus and method for accurate radioisotope counting in radio-LC is described. An chromatogram or a region of chromatogram is divided into multiple fractions. Each fraction is fed/delivered precisively into the transparent and effective section of the flow cell before conducting static counting. When a radioactive fraction is detected, the content of the flow cell is flushed out using either scintillant, solvent, or a gas. Thus, in some embodiments, the current invention includes following steps: a) flow, b) stop-flow, c) precise positioning of the fraction, d) static counting, and e) memory effect removal. In some embodiments Step c) can optionally be eliminated if a fine tube is positioned right at the beginning of the effective section of the flow cell to flush the flow cell with either a scintillant, solvent or gas. The sensitivity and accuracy are improved significantly.

In some embodiments of the invention, methods are provided for measuring radioactivity in an eluate from a chromatography column comprising the steps of:
 a) providing a liquid chromatograph comprising:
  (i) a chromatography column;
  (ii) a radioactivity detector having a flow cell, said flow cell having a radiation detection area;
  (iii) a conduit for flowing eluate from said chromatography column into said flow cell of said radioactivity detector;
  (iv) means for introducing a gas disposed in either:
   1) said conduit; or
   2) said flow cell; and
  (v) a controlable source of said gas;
 b) flowing said eluate from said chromatography column through said conduit and into said flow cell;
 c) stopping said flow of said eluate;
 d) counting the radioactivity of said eluate in said radiation detection area of said flow cell;
 e) flushing said flow cell with said gas to remove said eluate therefrom; and
 f) optionally repeating steps (b) through (e).

In some embodiments, said means for introducing said gas is disposed in said conduit. In other embodiments, said means for introducing said gas is disposed in said flow cell.

In accordance with the present invention, methods are also provided for measuring radioactivity in an eluate from a chromatography column comprising the steps of:
 a) providing a liquid chromatograph comprising:
  (i) a liquid chromatography column;
  (ii) a radioactivity detector having a flow cell, said flow cell having an input, an output, and a radiation detection area;
  (iii) a conduit for conducting eluate from said chromatography column to said input of said flow cell, said conduit having interposed therein means for introducing an agent solution into said conduit and mixing said agent solution with said eluate, to produce a mixed eluate-agent solution; and
  (v) means for introducing a gas into at least said radiation detection area to remove said eluate from said radiation detection area;
 b) either:
  (i) simultaneously flowing said eluate from said chromatography column and said agent solution through said introducing and mixing means, thereby flowing said mixed eluate-agent solution into said radiation detection area of said flow cell; or
  (ii) flowing said eluate from said chromatography column through said introducing means and into said radiation detection area of said flow cell;
 c) stopping said flow of said eluate or said mixed eluate-agent solution;
 d) counting the radioactivity of said eluate in said detection area of said flow cell in a static fashion;
 e) flushing at least said radiation detection area of said flow cell with said gas to remove said mixed eluate-agent solution therefrom;
 f) optionally flushing said radiation detection area of said flow cell with said agent solution; and
 g) optionally repeating steps (b) through (f).

Preferably, where a liquid flow cell is employed, step (b) comprises (i), and where a solid flow cell is employed, step (b) comprises (ii).

In some embodiments, said means for introducing said gas is disposed in said conduit between said mixing means and said radiation detection area. Preferably, said means for introducing said agent solution into said conduit comprises a mixing tee; and a conduit connecting said mixing tee to a source of said agent solution. In some embodiments, said means for introducing said gas is disposed in said conduit between said source of said agent solution and said mixing tee, and in other embodiments, said means for introducing said gas is disposed in said flow cell.

In some embodiments, the invention provides methods for measuring radioactivity in an eluate from a chromatography column comprising the steps of:
 a) providing a liquid chromatograph comprising:
  (i) a liquid chromatography column;
  (ii) a radioactivity detector having a solid flow cell, said flow cell having an input, an output, and a radiation detection area;
  (iii) a conduit for conducting eluate from said chromatography column to said input of said flow cell, said conduit having interposed therein means for introducing an agent solution into said conduit; and
  (v) means for introducing a gas into at least said radiation detection area to remove said eluate from said radiation detection area;
 b) flowing said eluate from said chromatography column through said introducing means and into said radiation detection area of said flow cell;
 c) stopping said flow of said eluate;
 d) counting the radioactivity of said eluate in said detection area of said flow cell in a static fashion;
 e) flushing at least said detection area of said flow cell with said gas to remove said mixed eluate-agent solution therefrom;
 f) optionally flushing said detection area of said flow cell with said agent solution; and
 g) optionally repeating steps (b) through (f).

In some embodiments, said means for introducing said gas is disposed in said conduit between said introducing means and said radiation detection area. In further embodiments, said means for introducing said agent solution into said conduit comprises:
 a tee; and
 a conduit connecting said tee to a source of said agent solution.

In further embodiments, said means for introducing said gas is disposed in said conduit between said source of said agent solution and said tee. In still further embodiments, said means for introducing said gas is disposed in said flow cell.

Also provided by the present invention are improvements to a stop-flow method for measuring the radioactivity of a radiolabeled sample solution, the method comprising:

(a) introducing a solution containing at least one radiolabeled species and an agent solution into a means for mixing said radiolabeled sample solution and an agent solution to produce a mixed sample-agent solution;

(b) flowing said mixed sample solution from said mixing means through a conduit and into a flow cell having a radiation detection area for detection of radioactivity;

(c) stopping said flow of said mixed sample solution;

(d) counting the radiation of the sample within said radiation detection area; and (e) optionally flushing at least said radiation detection area with a solvent or with said agent solution;

(f) optionally repeating steps (a) through (e); the improvement comprising:

after step (d), flowing into said flow cell a volume of gas that is at least as great as the volume of said sample in said flow cell to effect removal of said sample solution therefrom.

Also provided by the present invention are improvements to stop-flow method for measuring the radioactivity of a radiolabeled sample solution, the method comprising:

(a) introducing a sample solution containing a radiolabeled species into a conduit and into a solid flow cell having a radiation detection area for detection of radioactivity;

(b) stopping said flow of said sample solution;

(c) counting the radiation of said sample within said radiation detection area; and (d) optionally flushing at least said radiation detection area with a solvent; and (e) optionally repeating steps (a) through (d); the improvement comprising:

after step (c), flowing into said flow cell a volume of gas that is at least as great as the volume of said sample in said flow cell.

Also provided by the invention are methods for measuring radioactivity in an eluate from a chromatography column comprising the steps of:

a) providing a liquid chromatograph comprising:
  (i) a chromatography column providing an eluate therefrom;
  (ii) a radioactivity detector having a flow cell, said flow cell having a radiation detection area from which radiation is counted;
  (iii) a conduit for flowing said at least said eluate from said chromatography column into said flow cell, said conduit having disposed means for introducing an agent solution into said conduit and mixing said eluate and an agent solution to form a mixture thereof;
  (iv) means for introducing a gas into said flow cell; and
  (v) a controlable source of said gas;

b) flowing either:
  (i) said mixture of said agent solution and said eluate; or
  (ii) said eluate through said conduit and into said flow cell;

c) stopping said flow of said mixture;

d) flowing a volume of said agent solution through said introducing means and into said conduit means in an amount at least equal to the total volume of said conduit, said introducing means and said flow cell preceding said radiation detecting area, to ensure that said volume of eluate or mixed agent-sample solution residing in said conduit, said introducing means and said flow cell preceding said radiation detecting area is placed in said radiation detection area;

e) counting the radioactivity in said radiation detection area of said flow cell;

f) flushing said flow cell with said gas to remove said eluate therefrom; and g) optionally repeating steps (b) through (f);

wherein said means for introducing said gas is disposed within said radiation detection area of said flow cell. Preferably, said flow cell comprises:
  i) an exterior surface and an interior surface, said interior surface defining said radiation detection area;
  ii) an inlet through-aperture;
  iii) an exit through-aperture; each of said inlet and exit through-apertures connecting said radiation detection area with said exterior surface;
  iv) tubular means entering through said inlet through-aperture, and exiting through said exit through-aperture, and directing flow of said eluate through said radiation detection area; and
  v) flushing means for flushing the majority of said eluate from said radiation detection area, said flushing means comprising a flushing tube interposed within said tubular means, said flushing means being sealingly connected at one end to a source of gas, and open at the other end; said open end residing inside said tubular means at a point within said radiation detection area of said flow cell; and
  vi) means for entry of said flushing tube into said tubular means.

In some embodiments, the flow cell is a liquid flow cell, and in other embodiments, the flow cell is a solid flow cell. Preferably, where a liquid flow cell is employed, step (b) comprises (i), and where a solid flow cell is employed, step (b) comprises (ii).

In some embodiments, said tubular means is in the form of a coil. In further embodiments, the method further comprises a grounding wire interposed within said tubular means, preferably in the form of a helix.

In some embodiments, said tubular means is a thermoplastic polymer tube, preferably a teflon tube.

Some embodiments of the foregoing method further comprise the step of flushing said flow cell with a fluid, preferably after step (f).

In some embodiments of the foregoing method, said means for entry of said flushing tube is located on said tubular means at a point prior to said inlet through-aperture.

In further embodiments of the foregoing method, said flow cell further comprises a flushing line through-aperture connecting said exterior surface and said inlet through aperture, said flushing tube being disposed within said flushing line through-aperture, and wherein said means for entry of said flushing tube into said tubular means is located on said tubular means at a point within said inlet through aperture.

In still further embodiments of the foregoing method, said flow cell further comprises a flushing line through-aperture connecting said exterior surface and said interior surface, said flushing tube being disposed within said flushing line through-aperture, and wherein said means for entry of said flushing tube into said tubular means is located on said tubular means at a point within said radiation detection area.

In some embodiments, said flushing of said flow cell with said gas in step (f) comprises directing a steady stream of gas through said flushing means, or a discontinuous stream of gas through said flushing means, or pulses of gas through said flushing means.

Also provided in accordance with the present invention methods for measuring the radioactivity of an eluate from a liquid chromatography column, the method comprising:

(a) providing a liquid chromatograph comprising:
(i) a liquid chromatography column;
(ii) a radioactivity detector comprising a flow cell, said flow cell having a radiation detection area from which radioactivity is counted;
(iii) a conduit for conducting said eluate from said chromatography column into said flow cell of said radioactivity detector;
(iv) means for introducing an agent solution into said eluate interposed in said conduit;

b) simultaneously flowing said eluate from said chromatography column and said agent solution to produce a mixed eluate-agent solution in said conduit;

c) flowing said mixed eluate-agent solution into said flow cell;

d) stopping said flow of said eluate;

e) flowing a volume of said agent solution into said conduit that is sufficient to ensure that said mixed eluate-agent solution residing in said means for introducing said agent solution, in said conduit downstream of said means for introducing said agent solution, and in said flow cell preceding said radiation detecting region is placed into said radiation detection area of said flow cell;

f) counting the radioactivity of the solution in said radiation detection area in a static fashion;

g) optionally flushing said flow cell; and h) optionally repeating steps (b) through (f).

Preferably, said flushing in said step (g) comprises the steps of:

i) flushing said flow cell with a first fluid;

j) optionally flushing said flow cell with a second fluid; and k) optionally flushing said flow cell with a third fluid;
wherein each of said fluids is independently a gas, a solvent or an agent solution.

In some embodiments, said first fluid and said third fluid are each an inert gas, and said second fluid is a solvent or an agent solution, and in other embodiments said first fluid and said third fluid are each a solvent or an agent solution, and said second fluid is an inert gas. In some embodiments, the inert gas is helium or nitrogen.

In some embodiments of the foregoing methods, steps b–h are performed for every fraction eluted from said chromatography column. In other embodiments of the foregoing methods, steps b–h are performed only when a threshold amount of radioactivity is detected by said radioactivity detector.

In some embodiments of the foregoing methods, the liquid chromatograph further comprises a UV (i.e., ultraviolet)-visible absorbance detector. In some embodiments, steps b–h are performed only when a threshold amount of UV or visible electromagnetic radiation is detected by said UV-visible absorbance detector.

Also provided in accordance with the present invention are methods for measuring the radioactivity of an eluate from a liquid chromatography column, the method comprising:

(a) providing a liquid chromatograph comprising:
(i) a liquid chromatography column;
(ii) a radioactivity detector comprising a flow cell, said flow cell having a radiation detection area from which radioactivity is counted;
(iii) a conduit for conducting said eluate from said chromatography column into said flow cell of said radioactivity detector;
(iv) means for introducing an agent solution into said eluate interposed in said conduit;

b) flowing said eluate into said flow cell;

d) stopping said flow of said eluate;

e) flowing a volume of said agent solution into said conduit that is sufficient to ensure that said eluate residing in said means for introducing said agent solution, in said conduit downstream of said means for introducing said agent solution, and in said flow cell preceding said radiation detecting region is placed into said radiation detection area of said flow cell;

f) counting the radioactivity of the solution in said radiation detection area in a static fashion; and g) optionally flushing said flow cell;

h) optionally repeating steps (b) through (g).

In some embodiments of the foregoing methods, said flushing in said step (g) comprises the steps of:

i) flushing said flow cell with a first fluid;

j) optionally flushing said flow cell with a second fluid; and k) optionally flushing said flow cell with a third fluid;
wherein each of said fluids is independently a gas, a solvent or an agent solution.

In some embodiments of the foregoing methods, said first fluid and said third fluid are each an inert gas, and said second fluid is a solvent or an agent solution, and in other embodiments said first fluid and said third fluid are each a solvent or an agent solution, and said second fluid is an inert gas.

In some embodiments of the foregoing methods, steps b–h are performed for every fraction eluted from said chromatography column. In other embodiments of the foregoing methods, steps b–h are performed only when a threshold amount of radioactivity is detected by said radioactivity detector.

In some embodiments of the foregoing methods, the liquid chromatograph further comprises a UV (i.e., ultraviolet)-visible absorbance detector. In some embodiments, steps b–h are performed only when a threshold amount of UV or visible lightelectromagnetic radiation is detected by said UV-visible absorbance detector.

In some embodiments of the foregoing methods, step (b) further comprises simultaneously flowing said agent solution to produce a mixed eluate-agent solution in said conduit; and flowing said mixed eluate-agent solution into said flow cell.

Also provided by the present invention are methods for determining the radioactivity of an eluate from a liquid chromatography column, said method comprising:

a) providing a liquid chromatograph comprising:
(i) a liquid chromatography column;
(ii) pump means for pumping solvent through said chromatography column to produce an eluate;
(iii) a radioactivity detector comprising a flow cell, said flow cell having a radiation detection area from which radioactivity is counted;
(iv) a first conduit for introducing said eluate into said flow cell of said radioactivity detector;

(v) mixing means disposed in said first conduit;
(vi) a second conduit for introducing an agent solution into said mixing means;
(vi) pump means for pumping said agent solution; and
(vii) an optionally present UV-visible absorbance detector;

b) either:
  (1) pumping said eluate into said radiation detector so that at least part of said radiation detection area of said flow cell is occupied by said eluate; or
  (2) simultaneously pumping said eluate from said chromatography column and said agent solution through said mixing means so that at least part of said radiation detection area of said flow cell is occupied by said mixed eluate-agent solution;

c) stopping said flow of said eluate or said mixed eluate-agent solution;

d) pumping a volume of said agent solution through said second conduit and said mixing means and into said first conduit, said volume of agent solution being sufficient to ensure that said eluate or said mixed eluate-agent solution residing in said first conduit, said mixing means and said flow cell preceding said radiation detection area is placed into said radiation detection portion of said flow cell;

e) counting the radioactivity residing in the radiation detection portion of the flow cell in a static fashion;

f) flushing at least said radiation detection area of said flow cell with said agent solution; and g) optionally repeating steps (b) through (f).

In some embodiments, the flow cell is a liquid flow cell, and in other embodiments, the flow cell is a solid flow cell. Preferably, where a liquid flow cell is employed, step (b) comprises (2), and where a solid flow cell is employed, step (b) comprises (1).

In some embodiments, said second conduit comprises means for the introduction of a gas into said second conduit. In other embodiments, said method further comprises the step of flushing at least said radiation detection area of said flow cell with said gas, said gas flushing step being performed either immediately before or immediately after step (f).

In some embodiments, said mixing means disposed in said first conduit is a mixing tee. In further embodiments, said means for the introduction of a gas into said second conduit is a tee. In further embodiments, said agent solution comprises a scintillant.

In some embodiments, steps d–g are performed for every fraction eluted from said chromatography column. In other embodiments, steps d–g are performed only when a threshold amount of radioactivity is detected by said radioactivity detector. In other embodiments, steps d–g are performed only when a threshold amount of UV or visible light is detected by said UV-visible absorbance detector.

Also provided in accordance with the present invention are methods for accurately determining the radioactivity of an eluate from a liquid chromatography column, said method comprising:

a) providing a liquid chromatograph comprising:
  (i) a liquid chromatography column;
  (ii) pump means for pumping solvent through said chromatography column to produce an eluate;
  (iii) a radioactivity detector comprising a solid flow cell, said flow cell having a radiation detection area from which radioactivity is counted;
  (iv) a first conduit for introducing said eluate into said flow cell of said radioactivity detector;
  (v) means for introducing said agent solution into said first conduit disposed in said first conduit;
  (vi) a second conduit for introducing said agent solution into said introducing means;
  (vi) pump means for pumping said agent solution; and
  (vii) an optionally present UV-visible absorbance detector;

b) pumping said eluate from said chromatography column into said radiation detector so that a part of said radiation detection area of said flow cell is occupied by said eluate;

d) stopping said flow of said eluate;

e) pumping a volume of said agent solution through said second conduit and said means for introducing said agent solution into said first conduit, said volume of agent solution being sufficient to ensure that said eluate in said first conduit, said introducing means and said flow cell preceding said radiation detection area is placed into said radiation detection portion of said flow cell;

f) counting the radioactivity residing in the radiation detection portion of the flow cell in a static fashion;

g) flushing at least said radiation detection area of said flow cell with said agent solution; and h) optionally repeating steps (b) through (h).

In some embodiments, said second conduit comprises means for the introduction of a gas into said second conduit. In other embodiments, the foregoing methods further comprising the step of flushing at least said radiation detection area of said flow cell with said gas, said gas flushing step being performed either immediately before or immediately after step (g).

In some embodiments, said means for the introduction of a gas into said second conduit is a tee. In other embodiments, said agent solution is a solvent.

In some embodiments, steps d–g are performed for every fraction eluted from said chromatography column. In other embodiments, steps d–g are performed only when a threshold amount of radioactivity is detected by said radioactivity detector. In other embodiments, steps d–g are performed only when a threshold amount of UV or visible light is detected by said UV-visible absorbance detector.

Also provided by the present invention are improvements to a stop-flow method for measuring the radioactivity of a radiolabeled sample solution, the method comprising:

(a) introducing a sample solution containing at least one radiolabeled species and an agent solution into a means for mixing said sample solution and said agent solution to produce a mixed sample-agent solution;

(b) flowing said mixed sample-agent solution from said mixing means through a conduit and into a flow cell having a radiation detection area for detection of radioactivity;

(c) stopping said flow of said mixed sample-agent solution; and (d) counting the radioactivity of said mixed sample within said radiation detection area;

the improvement comprising:

after step (c) flowing a volume of said agent solution through said mixing means and into said conduit between said mixing means and said flow cell in an amount at least equal to the volume of said conduit and said mixing means, to ensure that said volume of mixed agent-sample solution residing in said conduit and said mixing means is placed in said radiation detection area prior to counting in step (d). In some embodiments, said method further comprises the step of:

(e) flushing said flow cell with said agent solution to remove said sample solution from said flow cell.

In some embodiments, said agent solution comprises a scintillant.

Also provided by the present invention are improvements to a stop-flow method for measuring the radioactivity of a radiolabeled sample solution, the method comprising:

(a) introducing a sample solution containing at least one radiolabeled species through a conduit and into a solid flow cell having a radiation detection area for detection of radioactivity, said conduit having interposed therein means for introducing an agent solution into said conduit;

(b) stopping said flow of said sample solution; and (c) counting the radioactivity of said sample solution within said radiation detection area; the improvement comprising:

after step (b) flowing a volume of an agent solution through said introducing means and into said conduit in an amount at least equal to the volume of said conduit and said introducing means, to ensure that said volume of sample solution residing in said conduit and said introducing means is placed in said radiation detection area prior to counting in step (c). In some embodiments, the method further comprises the step of:

(d) flushing said flow cell with said agent solution to remove said sample solution from said flow cell.

In some embodiments, said agent solution is a solvent.

Also provided by the present invention are improvements to a stop-flow method for measuring the radioactivity of a radiolabeled sample solution, the method comprising:

(a) introducing a sample solution containing at least one radiolabeled species and an agent solution into a means for mixing said sample solution and said agent solution to produce a mixed sample-agent solution;

(b) flowing said mixed sample-agent solution from said mixing means through a conduit and into a flow cell having a radiation detection area for detection of radioactivity;

(c) stopping said flow of said mixed sample-agent solution; and (d) counting the radioactivity of said mixed sample within said radiation detection area; the improvement comprising:

after step (d) flowing a volume of gas through said mixing means and into said conduit and said flow cell in an amount sufficient to remove said sample from said radiation detection area of said flow cell.

In some embodiments, the methods further comprise the step of:

(e) flushing said flow cell with said agent solution.

Also provided by the present invention are improvements to a stop-flow method for measuring the radioactivity of a radiolabeled sample solution, the method comprising:

(a) introducing a sample solution containing at least one radiolabeled species through a conduit and into a solid flow cell having a radiation detection area for detection of radioactivity, said conduit having interposed therein means for introducing an agent solution into said conduit;

(b) stopping said flow of said sample solution; and (c) counting the radioactivity of said sample solution within said radiation detection area; the improvement comprising:

after step (b) flowing a volume of a gas through said introducing means and into said conduit and said flow cell in an amount sufficient to remove said sample from said radiation detection area of said flow cell.

In some embodiments, the methods further comprise the step of:

(d) flushing said flow cell with said agent solution to remove said sample solution from said flow cell.

In some embodiments, said agent solution is a solvent.

Also provided by the present invention are methods for measuring radioactivity in an eluate from a chromatography column comprising the steps of:

(a) providing a liquid chromatograph comprising:
(i) a liquid chromatography column producing an eluate;
(ii) a radioactivity detector comprising a flow cell, said flow cell having a radiation detection area from which radioactivity is counted;
(iii) means for mixing said eluate and an agent solution to form a mixture thereof;
(iv) conduit means for directing said mixture into said flow cell; and
(v) means for introducing a gas into said flow cell; and
(vi) an optionally present UV-visible absorbance detector;

(b) flowing said mixture of said eluate and said agent solution through said conduit and into said radiation detection area of said flow cell;

(c) stopping said flow of said mixture;

(d) flowing a volume of said agent solution through said mixing means and into said conduit means in an amount at least equal to the total volume of said conduit, said mixing means and said flow cell preceding said radiation detection area, to ensure that said volume of mixed agent-sample solution residing in said conduit and said mixing means is placed in said radiation detection area;

(e) counting the radioactivity of said mixed sample within said radiation detection area; and (f) flushing at least said radiation detection of said area flow cell with said gas to remove sample mixture therefrom; and (g) optionally repeating steps (b)–(f).

In some embodiments, the methods further comprises the step of:

(h) flushing said flow cell with said agent solution.

In some embodiments, said step (g) is performed immediately preceding or immediately after step (f). In some embodiments, said agent solution is a solution comprising a scintillant.

In some embodiments, steps b–f are performed for every fraction eluted from said chromatography column. In other embodiments, steps b–f are performed only when a threshold amount of radioactivity is detected by said radioactivity detector. In other embodiments, steps b–f are performed only when a threshold amount of UV or visible light is detected by said UV-visible absorbance detector.

Also provided by the present invention are methods for measuring radioactivity in an eluate from a chromatography column comprising the steps of:

a) providing a liquid chromatograph comprising:
(i) a liquid chromatography column;
(ii) a radioactivity detector having a flow cell, said flow cell having an input, an output, and a radiation detection area;

(iii) a conduit for conducting eluate from said chromatography column, said conduit connecting said chromatography column and said input of said flow cell, said conduit having interposed therein means for introducing an agent solution into said conduit and mixing said agent solution with said eluate to produce a mixed eluate-agent solution;

(iv) means for flushing at least said radiation detection area with a gas to remove said eluate from said radiation detection area; and (v) an optionally present UV-visible absorbance detector;

b) simultaneously flowing said eluate from said chromatography column and said agent solution through said mixing means, thereby flowing said mixed eluate-agent solution into said radiation detection area of said flow cell;

c) stopping said flow of said eluate;

d) flowing a volume of agent solution through said mixing means and said conduit that is at least equal to the volume of said conduit, said mixing means and said radiation detector prior to said radiation detection area, to ensure that said volume of mixed agent-sample solution residing in said conduit, said mixing means and said radiation detector preceding said radiation detection area is placed in said radiation detection area;

e) counting the radioactivity of said mixed eluate-agent solution in said radiation detection area in a static fashion;

f) flushing at least said radiation detection area of said flow cell with said gas to remove said eluate therefrom;

g) optionally flushing at least said radiation detection area of said flow cell with said agent solution; and h) optionally repeating steps (b) through (g).

In some embodiments, said agent solution comprises a scintillant.

In some embodiments, steps b–g are performed for every fraction eluted from said chromatography column. In other embodiments, steps b–g are performed only when a threshold amount of radioactivity is detected by said radioactivity detector. In other embodiments, steps b–g are performed only when a threshold amount of UV or visible light is detected by said UV-visible absorbance detector.

Also provided by the present invention are methods for measuring radioactivity in an eluate from a chromatography column comprising the steps of:

(a) providing a liquid chromatograph comprising:
(i) a liquid chromatography column producing an eluate;
(ii) a radioactivity detector comprising a solid flow cell, said flow cell having a radiation detection area from which radioactivity is counted;
(iii) conduit means for directing said eluate into said flow cell, said conduit means having interposed therein means for introducing an agent solution into said conduit;
(v) means for introducing a gas into said flow cell; and
(vii) an optionally present UV-visible absorbance detector;

(b) flowing said mixture of said eluate through said conduit and into said radiation detection area of said flow cell;

(c) stopping said flow of said mixture;

(d) flowing a volume of said agent solution through said introducing means and into said conduit means in an amount at least equal to the volume of said conduit means, said introducing means, and said radiation detector preceding said radiation detection area to ensure that said volume of eluate residing in said conduit means, said introducing means and said radiation detector preceding said radiation detection area is placed in said radiation detection area;

(e) counting the radioactivity of said mixed sample within said radiation detection area; and (f) flushing at least said radiation detection of said area flow cell with said gas to remove sample mixture therefrom; and (g) optionally repeating steps (b)–(f).

In some embodiments the methods further comprises the step of:

(h) flushing said flow cell with said agent solution.

In further embodiments, said step (h) is performed immediately preceding or immediately after step (f). In further embodiments, said agent solution is a solution comprising a scintillant.

In some embodiments, steps b–f are performed for every fraction eluted from said chromatography column. In other embodiments, steps b–f are performed only when a threshold amount of radioactivity is detected by said radioactivity detector. In other embodiments, steps b–f are performed only when a threshold amount of UV or visible light is detected by said UV-visible absorbance detector.

Also provided by the present invention are methods for measuring radioactivity in an eluate from a chromatography column comprising the steps of:

a) providing a liquid chromatograph comprising:
(i) a liquid chromatography column;
(ii) a radioactivity detector having a flow cell, said flow cell having an input, an output, and a radiation detection area;
(iii) a conduit for conducting eluate from said chromatography column, said conduit connecting said chromatography column and said input of said flow cell, said conduit having interposed therein means for introducing an agent solution into said conduit;
(v) means for flushing at least said radiation detection area with a gas to remove said eluate from said radiation detection area; and
(vi) an optionally present UV-visible absorbance detector;

b) flowing said eluate from said chromatography column through said conduit and into said radiation detection area of said flow cell;

c) stopping said flow of said eluate;

d) flowing a volume of agent solution through said introducing means and said conduit that is at least equal to the total volume of said conduit, said mixing means and said radiation detector preceding said radiation detection area, to ensure that said volume of eluate residing in said conduit, said mixing means and said radiation detector preceding said radiation detection area is placed in said radiation detection area;

e) counting the radioactivity of said mixed eluate-agent solution in said radiation detection area in a static fashion;

f) flushing at least said radiation detection area of said flow cell with said gas to remove said eluate therefrom;

g) optionally flushing at least said radiation detection area of said flow cell with said agent solution; and h) optionally repeating steps (b) through (g).

In some embodiments, steps b–g are performed for every fraction eluted from said chromatography column. In other embodiments, steps b–g are performed only when a threshold amount of radioactivity is detected by said radioactivity detector. In other embodiments, steps b–g are performed only when a threshold amount of UV or visible light is detected by said UV-visible absorbance detector.

Also provided in accordance with the present invention is a system for measuring radioactivity in a liquid eluate from a chromatography column, the system comprising:

- a transparent detection tube;
- an inlet conduit for supplying eluate to the detection tube;
- an eluate conduit for supplying eluate to the inlet conduit;
- an eluate valve disposed in the eluate conduit, the eluate valve opening to enable flow of the eluate from the eluate conduit through the inlet conduit and into the detection tube in response to a signal from a controller;
- an agent conduit for supplying a liquid agent to the inlet conduit;
- an agent valve disposed in the agent conduit, the agent valve opening to enable flow of the agent from the agent conduit through the inlet conduit and into the detection tube in response to a signal from the controller; and
- at least one photomultiplier tube having an element disposed proximate the detection tube for measuring a parameter related to radioactivity of the eluate;
- the controller being in informational communication with the eluate valve, the agent valve, and the photomultiplier tube to facilitate sequentially a flow stage, a push stage, a measuring stage, and a flush stage such that:
  - each one of the eluate valve and the agent valve are open to define the flow stage during which the eluate and the agent flow into the inlet conduit and into a portion of the detection tube;
  - the eluate valve is closed and the agent valve is open to define the push stage during which the eluate disposed in at least a portion of the inlet conduit is forced into the detection tube by the agent;
  - each one of the eluate valve and the agent valve is closed to define the measuring stage during which the eluate in the detection tube is substantially stationary, whereby the radioactivity measurement is performed on substantially stationary eluate for a time period; and
  - the eluate valve is closed and the agent valve is open to define a flush stage in which the detection tube is flushed of the eluate by a flow of the agent, whereby measurement of the radioactivity is improved by removing residual eluate from the detection tube, whereby subsequent to the flush stage the system is in condition to initiate another flow stage.

In some embodiments, the foregoing system further comprises an eluate pump disposed in the eluate conduit for pumping the eluate and an agent pump disposed in the agent conduit for pumping the agent. In some embodiments, the detection tube is a coil.

In further embodiments, the eluate inlet and the agent inlet form a pair of inlet legs of a tee connector, and the inlet conduit form an outlet leg of the tee connector.

In still further embodiments, the agent includes a scintillant that produces flashes in response to receiving radiation from the eluate, whereby the photomultiplier tube senses the flashes to measure the radioactivity of the eluate.

In still further embodiments, the system further comprising a scintillant disposed outside of the detection tube, the scintillant produces flashes in response to receiving radiation from the eluate through the detection tube, whereby the photomultiplier tube senses the flashes to measure the radioactivity of the eluate.

In still further embodiments, the system further comprising a gas source in flow communication with the agent conduit and a gas valve for controlling the flow of gas into the agent conduit, the gas valve opening to substantially purge the detection tube of liquid, thereby augmenting the flush stage.

In some embodiments, the gas valve is open prior to the flush stage. In further embodiments, the gas valve is open subsequent to the flush stage. In further embodiments, the gas valve remains continuously opened during purging. In still further embodiments, the gas valve is cycled during purging to provide gas pulses.

In still further embodiments, the system further comprising a gas source in flow communication with the detection tube and a gas valve for controlling the flow of gas into the agent conduit, the gas valve opening to substantially purge the detection tube of liquid, thereby augmenting the flush stage, the gas source having an inlet in the detection tube to define a purgeable portion of the detection tube and an unpurgeable portion of the detection tube, the purgeable portion of the detection tube being substantially purged of liquid upon the opening of the gas valve.

In still further embodiments of the system, eluate disposed in the unpurgeable portion of the detection tube is pushed to a distal end of detection tube during the push stage so as to be disposed in the detection tube during a second measuring stage.

Also provided by the present invention is a system for measuring radioactivity in a liquid eluate from a chromatography column, the system comprising:

- a transparent detection tube;
- an inlet conduit for supplying eluate to the detection tube;
- an eluate conduit for supplying eluate to the inlet conduit;
- an eluate valve disposed in the eluate conduit, the eluate valve opening to enable flow of the eluate from the eluate conduit through the inlet conduit and into the detection tube in response to a signal from a controller;
- an agent conduit for supplying a liquid agent to the inlet conduit;
- an agent valve disposed in the agent conduit, the agent valve opening to enable flow of the agent from the agent conduit through the inlet conduit and into the detection tube in response to a signal from the controller;
- at least one photomultiplier tube having an element disposed proximate the detection tube for measuring a parameter related to radioactivity of the eluate; and
- a gas source for purging at least a portion of the detection tube of liquid; whereby the eluate is stopped in the detection tube for a time period during which radioactivity measurements are performed, the gas source purging at least a portion of the detection tube subsequent to such radioactivity measurements.

In some embodiments of the system, the gas source includes a gas inlet disposed in the agent conduit, whereby at least a portion of the inlet conduit and the detection tube are purged upon opening of the gas valve.

In further embodiments, the gas source includes an inlet disposed within the detection tube to define a purgeable portion of the detection tube and an unpurgeable portion of the detection tube, the purgeable portion of the detection tube being substantially purged of liquid upon the opening of the gas valve.

In still further embodiments, eluate disposed in the unpurgeable portion of the detection tube is pushed to a distal end of detection tube so as to be disposed in the detection tube during a second measuring stage.

In further embodiments, the present invention provides improvements to flow cells for the detection of a radioactive species in a liquid sample, wherein said flow cell has a tubular means for conducting said liquid sample through said flow cell; the improvement comprising a grounding wire disposed within said tubular means in the form of a helix or coil.

In still further embodiments, the invention provides a flow cell for detection of a radiolabeled species in a liquid sample, said flow cell comprising:

i) an exterior surface and an interior surface, said interior surface defining said radiation detection area;

ii) an inlet through-aperture;

iii) an exit through-aperture; each of said inlet and exit through-apertures connecting said radiation detection area with said exterior surface;

iv) tubular means entering through said inlet through-aperture, and exiting through said exit through-aperture, and directing flow of said eluate through said radiation detection area; and v) a grounding wire interposed within said tubular means, said grounding wire being in the form of a helix.

In some embodiments of each of the foregoing methods, systems and flow cells of the invention, the flow cell can be either a liquid flow cell or a solid flow cell. Preferably, in some embodiments of each of the methods and systems of the invention the flushing gas is an inert gas, preferably nitrogen or helium.

In some embodiments of each of the foregoing methods of the invention, flushing with said gas comprises directing a steady stream of gas. In other embodiments of each of the foregoing methods of the invention, said flushing with said gas comprises directing a discontinuous stream of gas. In other embodiments of each of the foregoing methods of the invention, said flushing with said gas comprises flushing with pulses of gas. In one particularly preferred embodiment of each of the foregoing methods of the invention, the flushing with gas in the methods of the invention comprises the steps of:

i) flushing said flow cell with a first fluid;

j) optionally flushing said flow cell with a second fluid; and k) optionally flushing said flow cell with a third fluid; wherein each of said fluids is independently a gas, a solvent or an agent solution. In some embodiments, said first fluid and said third fluid are each an inert gas, and said second fluid is a solvent or an agent solution, and in other embodiments said first fluid and said third fluid are each a solvent or an agent solution, and said second fluid is an inert gas.

In some embodiments of the methods and systems of the invention, the liquid chromatograph will include a UV-visible absorbance detector.

In some embodiments of the methods and systems of the invention, the agent solution comprises a scintillant.

BRIEF DESCRIPTIONS OF DRAWINGS

Figure 1:
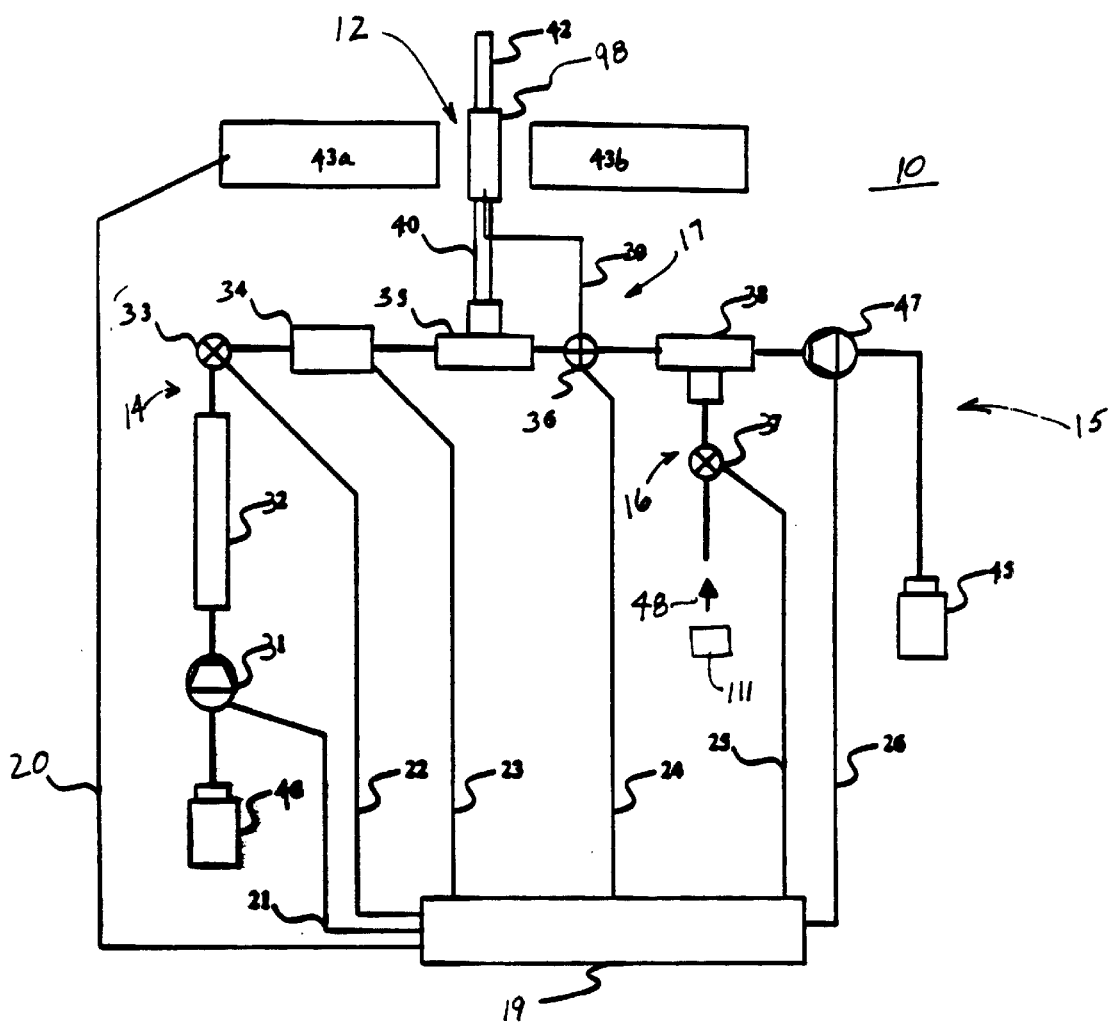
FIG. 1 is a schematic of a illustrating an aspect of the present invention.
Figure 6:
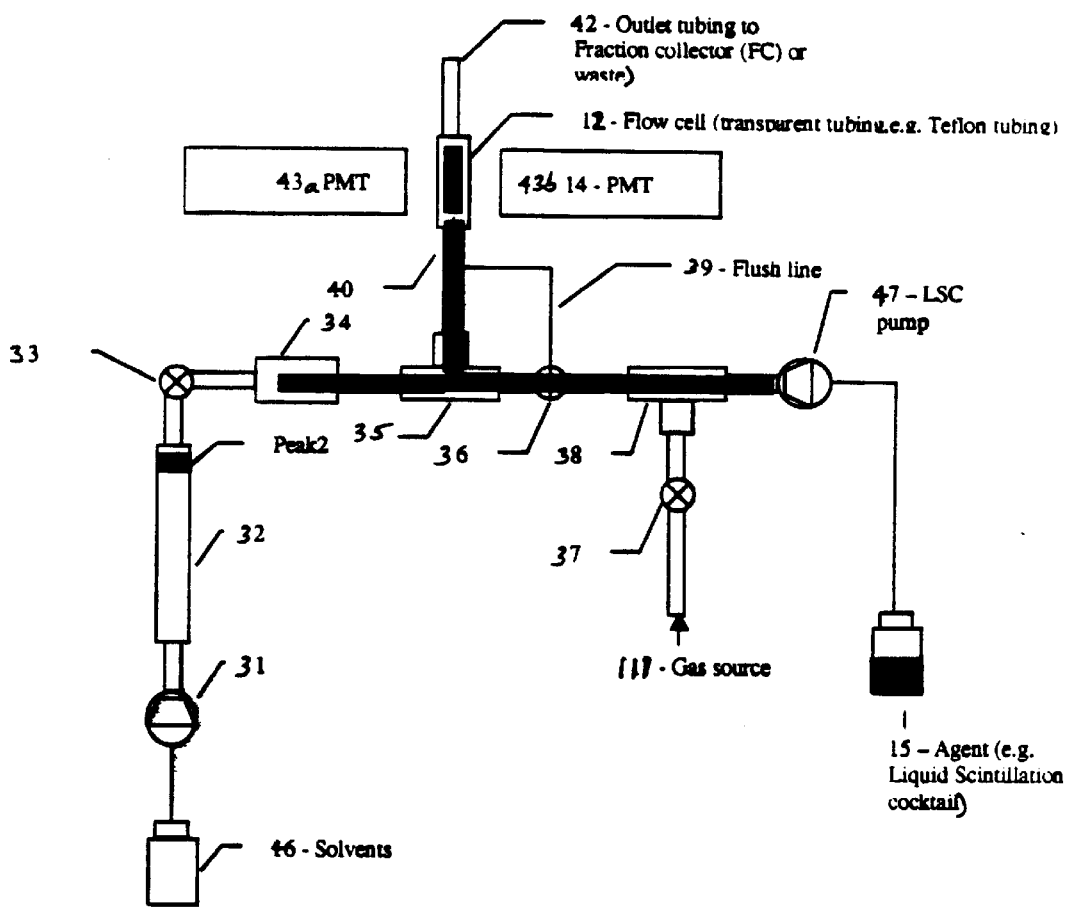
Figure 7:
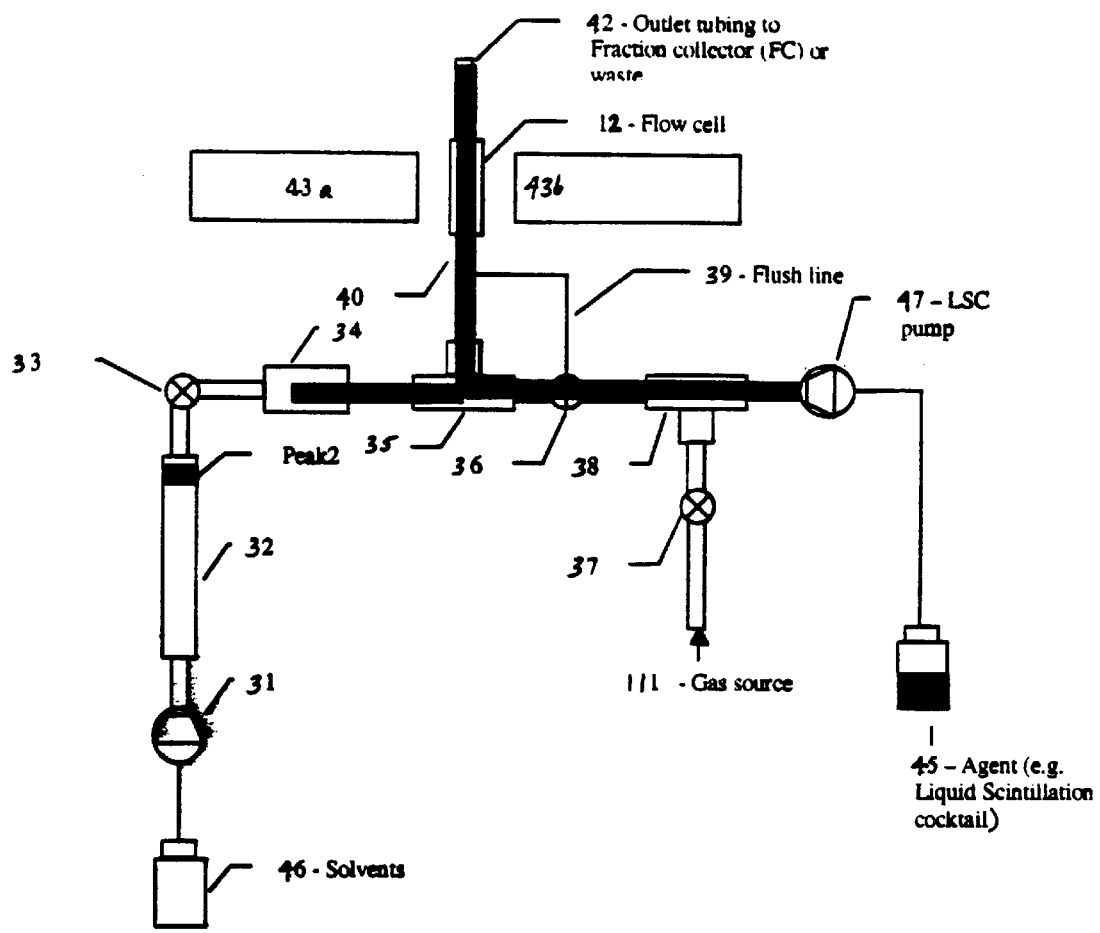
Figure 8:
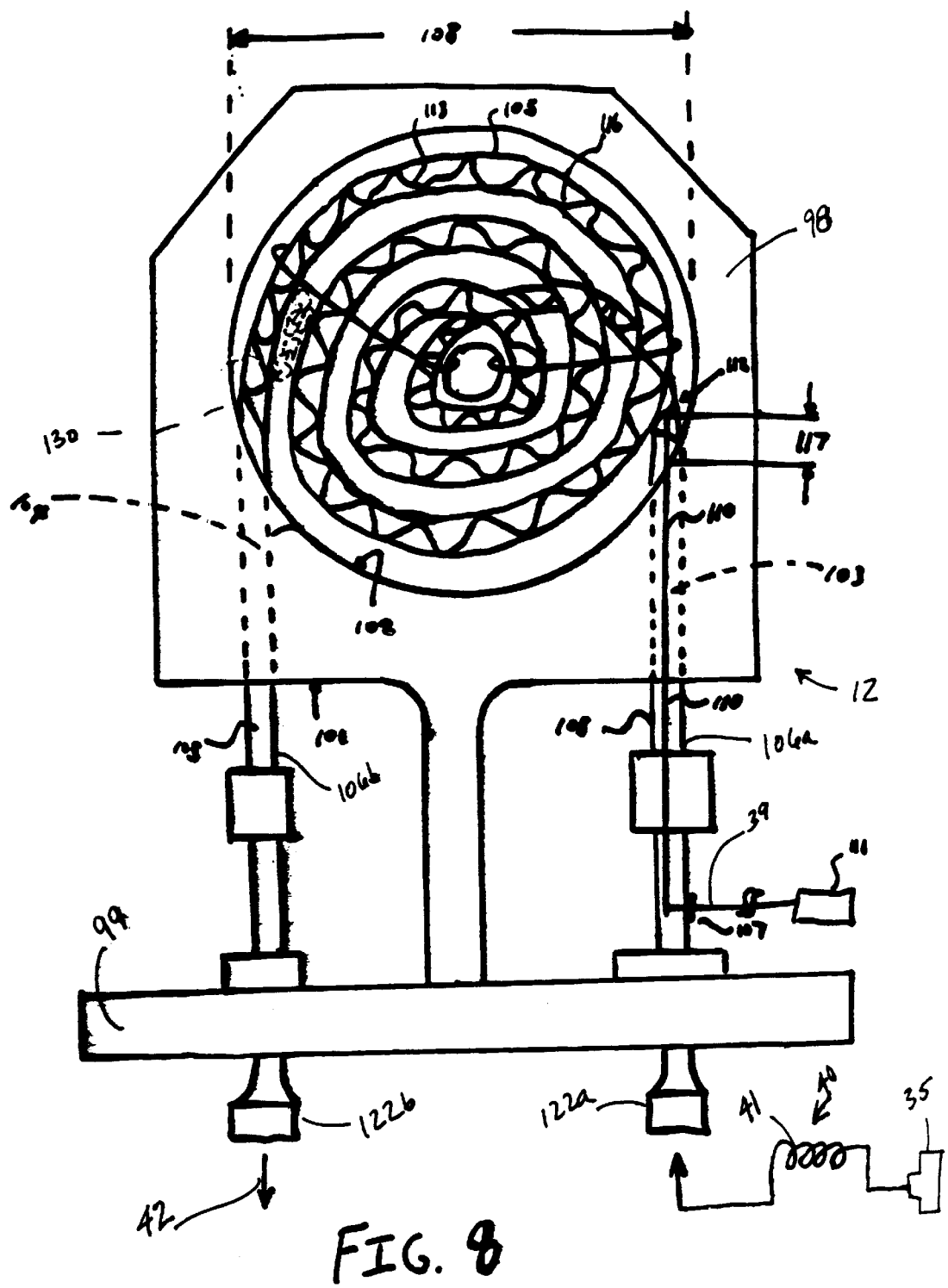

FIG. 6 a simplified schematic similar to that shown in FIG. 1 illustrating the push-in phase, in which the fraction is precisely positioned in the flow cell;

FIG. 7 a simplified schematic similar to that shown in FIG. 1 illustrating the flushing phase in which the flow cell is flushed to remove the memory effect with a gas and/or an agent; and FIG. 8 is a diagram of a flow cell according to another aspect of the invention.

DESCRIPTION OF PREFERRED EMBODIMENTS

According to aspect of the present invention, a system and a method for measuring radioactivity in a liquid eluate is provided. Particular embodiments of the present invention are described herein and illustrated in the figures. The present invention is not limited to the particular embodiments described herein, but rather the present invention encompasses any combination or variation of components in light of the present disclosure.

In this regard, as illustrated schematically in FIG. 1, a system 10 for measuring radioactivity in a liquid eluate includes a flow cell 12, an eluate delivery system 14, an agent delivery system 15, a gas delivery system 16 (optional), and a controller 19. Flow cell 12 may, according to another aspect of the present invention, optionally include a flushing system 17, which includes a flushing tube 110.

Referring to FIG. 8 to illustrate an embodiment of an aspect of the present invention, flow cell 12 includes a body 98, an exterior surface 101, an interior surface 102, an inlet through-aperture 103, an exit through-aperture 104, and a tubular means, such as tube 105. According to another aspect of the present invention, a flushing means, such as flushing tube 110, and means for entry for flushing means, such as a flushing apparatus fitting 107 may be employed. In the embodiment shown in FIG. 8, flow cell 12 is a liquid flow cell.

Body 98 preferably is formed from a block of aluminum into which through apertures 103 and 104 and surfaces 101 and 102 may be fabricated. The present invention is not limited to the particular geometry shown in the figures, but rather encompasses any geometry consistent with achieving the overall functions apparent from the disclosure. Body 98 includes a support 99 to which it is mechanically coupled by any conventional means. A pair of tube supports 106a and 106b, each of which preferably is a substantially rigid tube in which a portion of tube 105 is disposed, are mechanically coupled between support 99 and apertures 103 and 104, respectively. Thus, supports 106a and 106b protect and guide tube 105. A pair of fitting 122a and 122b are mechanically coupled to the underside of support 99 opposite body 98 to receive tube 105. Fitting 122b at the outlet of tube 105 may be coupled to a fraction collector or to disposal. The mechanical coupling referred to herein encompasses any conventional means, such as threaded connections.

Interior surface 102, which preferably is defined by a through-hole formed entirely through the body 98, defines a radiation detection area 108. Thus, flow cell 12 may form a pair of radiation detection areas 108 on opposing sides thereof if it is desired to employ a pair of radiation detectors 43a and 43b, which preferably are photo multiplier tubes, as illustrated in FIG. 1, as will be understood by persons familiar with measurement of radiation and the corresponding detection and measuring instruments. In this regard, radiation detection area 108 provides uninterrupted access to tube 105 for detectors 43a and 43b. Radiation detection area 108 is connected to exterior surface 101 by inlet through-aperture 103, and exit through-aperture 104.

Thus, tube 105 enters radiation detection area 108 through inlet aperture 103 and exits through exit aperture 104. A radiation detection region of tube 105 is defined by the accessible portion of tube 105 within area 108. The radiation detection region may be defined by the entire portion of tube 105 within area 108 (that is, all of tube 105 between the outlet of inlet aperture 103 and the inlet of outlet aperture 104), or alternatively may be defined by the region that is sensed or measured by the particular PMT configuration employed, or like definition.

Tube 105 directs the flow of eluate therethrough to enable radioactivity measurement by PMTs 43a and 43b within area 108. The flow cell 12 illustrated in FIG. 8 is a liquid-type, in which the eluate includes a scintillant mixed therewith, although the present invention encompasses a solid-flow type in which the eluate passes through tube 105 without a scintillant mixed therein. The solid-flow type of flow cell employs a solid scintillant 130 disposed proximate tube 105, as shown diagrammatically in FIG. 8 in dashed lines. Solid scintillant 130 may be disposed about tube 105 by any means and in any configuration, as will be understood by persons familiar with flow cell technology in light of the present disclosure. Solid scintillant is illustrated in FIG. 8 as granular, and the present invention encompasses any form of scintillant.

Tubular means 105 may be formed of any material, and preferably is formed of a material that does not react or minimally reacts with the eluate and that permits the detection of radioisotopes contained within tube 105. In this regard, tube 105 preferably is transparent, especially within its radiation detection region, when employed in a liquid-flow cell configuration to facilitate radiation measurement by PMTs 43a and 43b. As explained more fully herein, eluate is preferably admixed with an agent prior to flowing through radiation detection area 108 in the liquid flow-cell configuration. In a solid-flow cell configuration, tube 105 may be transparent or opaque, according to the particular configuration of radiation measurement equipment. Further, the present invention encompasses employing any type of radiation detection and measurement equipment.

Preferably, tube 105 is a thermoplastic polymer tube. Preferable thermoplastic tubes are Teflon tubes. The invention, however, is not limited thereto, but rather encompasses employing any suitable material. Preferably, tube 105 is in the form of a spiral or coil with a depth (that is, in a direction perpendicular to the plane of the paper as oriented in FIG. 8) of a single tube width, which provides tight packing of tube 105. Tube 105 is shown in a loose spiral configuration in FIG. 8 for clarity, and tube 105 preferably is wound tightly about its center such that adjacent revolutions are in contact with each other.

Tube 105 is coupled to an inlet conduit 40, which may be coupled to inlet fitting 122a, and an outlet conduit 42, which may be coupled to outlet fitting 122b. Conduits 40 and 42 are indicated schematically on FIGS. 1 and 8. Inlet conduit 40 preferably is coupled to a tee 35, which receives eluate on a first end and agent on the second end, according to the control of the respective valves, as described more fully below. Inlet conduit 40, which preferably is formed of stainless steel tubing, is formed into a coil 41, as shown schematically in FIG. 8, to promote mixing and to increase residence time of the eluate-agent mixture.

According to another aspect of the present invention, flow cell 12 may include a grounding wire 113 disposed within tube 105. Grounding wire 113 disperses electrostatic charge that may accumulate within tube 105, such as for example by the movement of eluate through the tube. Preferably, grounding wire 113 is in the form of a helix, although the present invention encompasses virtually any other shape of wire 113, such as straight or any other configuration as will be understood by persons familiar with such apparatus. The coiled or helical configuration of grounding wire 113 provides for increased contact between the grounding wire and the interior wall of the tube, thus dissipating more static charge that results from the flow of sample through the tube. Such static may pose serious measurment problems because discharges of static can be read by the photomultiplier tubes of the detector as a signal from a scintillant, leading to artificially inflated radioactivity counts.

Further, the present invention encompasses disposing wire 113 through the detection region of tube 105 or in any part there, such as proximate the inlet, and/or the outlet, of the detection region of tube 105. Wire 113 is shown in FIG. 8 as disposed throughout the detection region of the tube 105 for simplicity. Grounding wire 113 may contact the flushing tube 110 and/or flushing fitting 107 to provide a ground therefor, or may be coupled to any other convenient metallic surface according to the particular configuration employed, as will be apparent to persons generally familiar with relevant technology in light of the present disclosure.

Tube 105, and particularly at least a portion of its detection region, preferably is flushed of eluate after the measuring stage of operation to prepare for a subsequent stop-flow cycle, as described below. According to another aspect of the present invention, a flushing apparatus 17 is provided that is capable of delivering either a liquid or gaseous flushing material to tube 105 proximate its detection region. Flushing apparatus 17 preferably includes a flushing tube 110 disposed within tube 105.

Preferably, flushing tube 110 is sealingly connected at one end to a source of gas 111, and has an opposing open end 112 that is disposed within tube 105. Open end 112, out of which the liquid or gaseous flushing agent flows, may be disposed either upstream or prior to the inlet of aperture 103 (not shown in the Figures), within inlet through-aperture 103 (not shown in the Figures), or within radiation detection region of tube 105 (the latter of which is shown in FIG. 8). In this regard, flushing tube 110 preferably is disposed within inlet aperture 103. As shown in the configuration in which open end 112 is disposed within the detection region of tube 112, open end 112 defines a purgeable portion 116, which is downstream of open end 112, and an unpurgeable portion 117, which is disposed upstream of open end 112, of tube 105.

Flushing tube 110 may be joined with tube 105 by any conventional equipment. For example, flushing fitting 107 may include tube fittings interrupting tube 105 such that flushing tube 110 may be disposed therein from a tee. In this regard, flushing fitting 107 is shown schematically in FIG. 8, and encompasses any conventional configuration.

Source of gas 111 may hold any gas that does not react or minimally reacts with eluate 109, agent 113, or mixture thereof. Preferably, gas source 111 contains a gas that is inert. More preferably, the gas is selected from a group that includes nitrogen and helium, and any pressure suitable for flushing or purging tube 105. As shown schematically in FIG. 1, a gas valve 36 may be employed to a steady stream of gas, a discontinuous stream of gas, or pulses of gas. Preferably, gas enters flow cell 12 in a pulsed flow to facilitate purging of the eluate and/or agent. In this regard, the gas may remove the liquid from the purgeable portion 116 of tube 105 at the appropriate stage. In addition, in some embodiments, more than one gas can be used in seriatum to flush the cell.

Any type of radiochemical detector, indicated in FIG. 1 by reference numerals 43a and 43b, capable of detecting radio-isotopes may be employed as a radioisotope detection means, which preferably includes a conventional a photomultiply tube.

Referring again to FIG. 1, eluate delivery system 14 includes a supply of solvent that is to be fractionated, an eluate pump 31, a liquid chromatography ("LC") system 32, and an eluate valve 33. LC column 32 separates the eluate according to conventional principles. Any chromatograph capable of measuring fractionated liquids may be employed. Further, aspects of the present invention, for example flow cell 12, and the flushing and purging stages (for example) do not depend on the use of an LC, and the invention should not be limited thereto, but rather should encompass any use thereof. As with all of the components listed herein, conventional piping connects the components as shown in the figures unless otherwise described.

Pump 31 and eluate valve 33 are in informational communication with controller 19 via lines 21 and 22, respectively. At an outlet (that is, disposed at the downstream side) of eluate valve 33, a detector 34 is disposed. Detector 34 encompasses any of on-line LC detectors, such as an ultraviolet detector, or other conventional detectors. Detector 34 is in informational communication with controller 19 via line 23.

Agent delivery system 15 includes an agent source 45 and an agent pump 47, which is in informational communication with controller 19 via line 26. Agent may be any conventional liquid suitable for the use described herein. For liquid flow-cell configurations, the agent includes (or has a system for introduction and mixing of) a conventional scintillant suitable for use with detectors 43a and 43b and the particular eluate that is to be measured.

Gas delivery system 16 includes gas source 48, gas valve 37, and an inlet tee 38 which is coupled with the agent piping. Preferably, gas source 48 is compressed gas. Gas valve 37 is in informational communication with controller 19 by line 25. Flushing system 17 includes a includes a switching valve 36 and flushing apparatus 17. Switching valve is in informational communication with controller 19 via line 24, and has a closed position in which switching valve 36 prevents the flushing fluid (which may be gas, liquid agent, or both) from flowing, a first open position in which the flushing fluid flows into the second leg of tee 35 to facilitate flushing of inlet conduit 40 and all of tube 105, and a second open position in which the flushing fluid flows through piping 39 into flushing apparatus 17 to flush the purgeable portion 116 of tube 105.

Controller 19 controls the pumps, valves, and performs data acquisition through signal lines 20 through 26. Controller 19 may be any control system that is capable of coordinating the flow of eluate, agent, and gas through the radioactivity measuring system. Preferably, control arrangement 19 is selected form a group including a programmable logic controller, a personal computer, a controller incorporated into the chromatograph, a controller incorporated into the chromatography column, combinations thereof, or any other conventional controller.

A stop-flow radioactivity counting method, according to another aspect of the present invention, will be described in conjunction with a description of the operation of system 10. System 10 may be operated according to several different modes of operation according to the present method. A first mode is to measure radioactivity by counting every fraction eluting from the entire LC run (that is, from eluate delivery system 14). A second mode is to count only the peaks which exceed a predefined criteria, which may be determined by threshold values or other algorithms, as will be understood by persons familiar with radioactivity measurements in light of the present disclosure. A third mode is to count only the regions of interest of the LC run.

Figure 2:
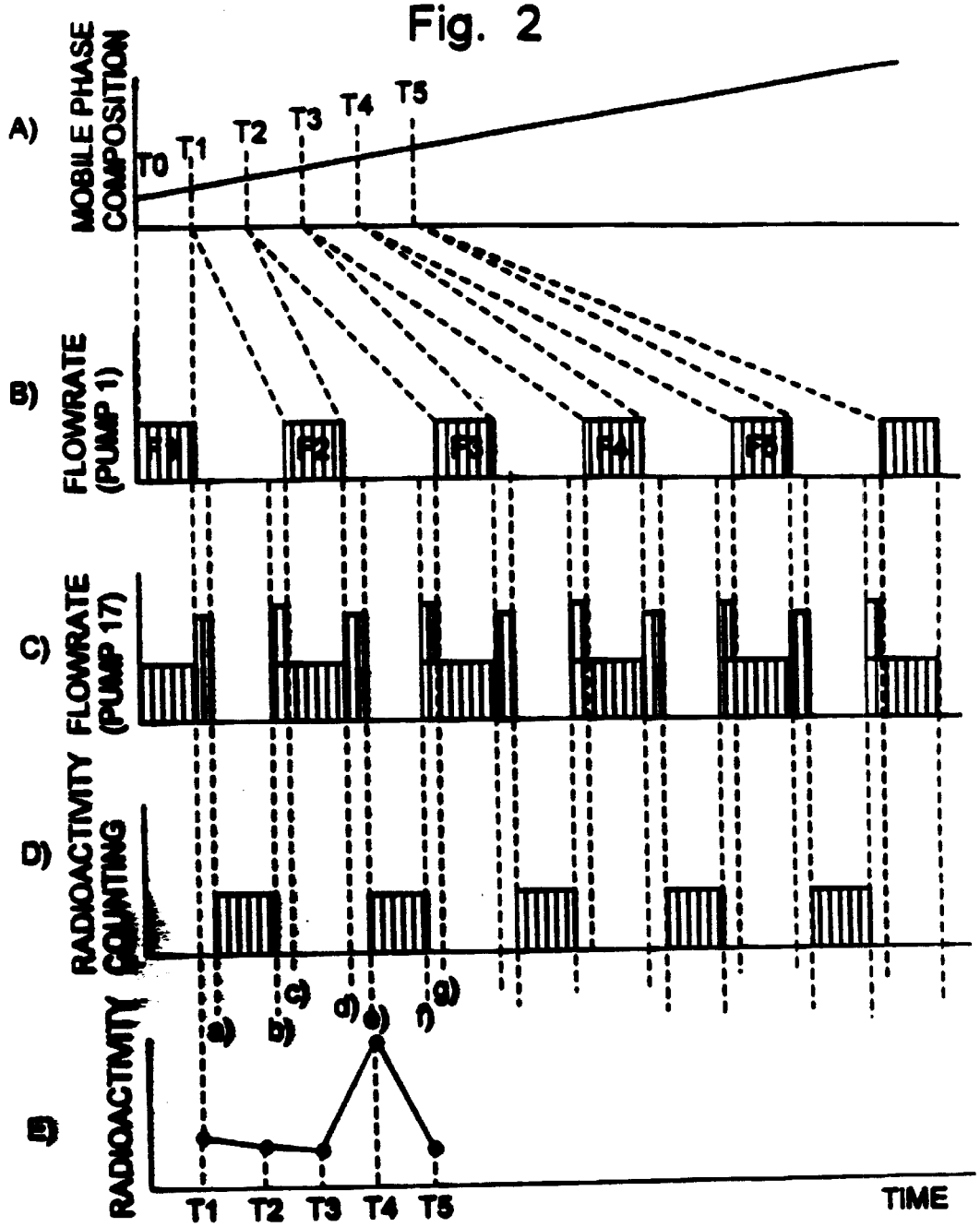
FIGS. 2A through 2E are diagrams illustrating the phases of a method according to as aspect of the present invention employing a first operating mode.

Many variations of this stop-flow counting method are possible without departing from the spirit of the present invention. FIG. 2 illustrates stop-flow radioactivity counting method for counting every fraction of a entire LC run. FIG. 2 shows the beginning part of the operation sequences for a typical stop-flow radioactivity counting method of present invention with a predefined time interval for fractions. FIG. 2A shows the change of the mobile phase composition in pump 31 under a linear gradient. If a isocratic mobile phase is used, the line in FIG. 2A becomes a horizontal line parallel to the time (horizontal) axis. FIG. 2B shows the flow rate of mobile phase delivered by eluate pump 31. FIG. 2C shows the flow rate of agent pump 37. FIG. 2D shows the radioactivity counting operation in the radioactivity detectors 43a and 43b. FIG. 2E shows the results of the stop-flow radioactivity counting representing for the radioactivity in fractions F1, F2, F3, F4, and F5.

A particular stop-flow counting method may comprise five phases for each fraction subjected to stop-flow counting: flow, stop-flow, push-in, static counting, and flushing. The flow phase is to collect the eluate or eluate mixture with liquid scintillant (for a liquid cell) into flow cell 12. Thus, eluate pump 31 is activated and eluate valve 33 is open during the flow stage. For the configurations employing a liquid flow cell, agent pump 47 pumps the agent (which contains the scintillant) and switching valve enables the agent to flow to the tee 35. Controller 19 and pumps 31 and 47 control the ratios of the eluate and agent according to conventional principles. The liquid eluate (or eluate agent mixture) is pumped into inlet conduit 40 and, depending on the volume of the particular configuration of the components, possibly into at least a portion of tube 105.

The stop-flow phase is to stop the flow of LC (liquid chromatograph) and the scintillant and prevent any degradation in resolution for those component still residing in the column 32. Eluate pump 31 is switched off, and eluate valve 33 may be closed. Agent pump 47, however, is powered to move the eluate (or eluate agent mixture) from tee 35 and through inlet conduit 40 and into the detection region of tube 105. Thus, the push-in phase positions the entire fraction of eluate into the flow cell 12, and preferably mostly into the detection region of tube 105, to facilitate the counting operation to be performed thereon. The push-in phase is advantageous if the flushing phase, which is described below, is performed through mixing tee 35 and inlet conduit 40. The push-in phase is optional if the flushing phase is performed through flushing apparatus 17.

The measuring or static counting phase is to measure the radioactivity inside the detection region of tube 105 by PMTs 43*a* and 43*b*. During the measuring phase, each of the pumps are switched off such that the liquid within tube 105 is static (that is, has no net flow).

The flushing stage is to remove any radioactivity of the counted fraction to diminish or eliminate the radioactivity carried over to next fraction to be measured. The flushing phase can be performed through mixing tee 35 and inlet conduit 40 or through flushing apparatus to directly flush cell content from the beginning part of the flow cell 11. For flushing through mixing tee 35, agent pump 47 is switched on and switching valve 36 directs the anent flow through tee 35 while eluate pump 31 is in the off position. For flushing through flushing apparatus 17, agent pump 47 is switched on and switching valve 36 directs the agent flow through piping 39 and into flushing tube 110.

Referring again to FIG. 2 to provide a more detailed description of the phases, before the sample is injected, valve 33 is turned to the open position and eluate pump 31 is at the initial conditions of the liquid chromatography. The gradient is divided into equal or different time intervals or fractions for counting radioactivity by radioactivity detectors 43*a* and 43*b* in a stationary manner (for example, the first five fractions (F1 through F5) are shown in FIG. 2A). Fraction F1 contains the eluate between time points T0 and T1. Fraction F2 is the eluate collected from time points T1 through T2, etc.

The flow phase is shown as between time points T0 and T1 in FIG. 2. When a sample is injected (the sample injector is not shown in the figures), eluate pump 31 starts the solvent elution or gradient. If a liquid cell is used, pump 47 also starts pumping liquid scintillation fluid which flows through mixing tee 38, and valve 36. The sample is pushed onto LC 32 for fractionation. The eluate from the column 32 flows through detector 34, and is mixed with scintillant (if a liquid cell is used) in mixing tee 35. The mixture of the eluate and scintillant flows through inlet conduit 40 and into the transparent portion of the flow cell 12. If a solid cell is used, pump 47 does not pump anything during the flow phase.

Regarding the stop phase, when time point T1 is encountered, controller 19 will send a stop-flow signal to eluate pump 31 to stop the flow of the mobile phase through signal line 20, and both flow and gradient are stopped or paused. Approximately simultaneously, the controller 19 sends a signal through line 21 to turn the valve 33 to the closed position in order to stop the flow of mobile phase upstream of valve 33 completely.

The push-in phase is illustrated as between time points T1 and a). Agent pump 47 pumps at the same flowrate or a different flowrate to push in the possible radioactivity still residing inside the mixing tee 35 and inlet conduit 40 until the whole fraction is precisely positioned in the transparent part of the flow cell 12. At such a point, the internal space between mixing tee 35 and the beginning part of the transparent portion of flow cell 12 is filled with fresh scintillant and contains no eluate which might contain radioactivity.

Regarding the static counting phase, once the flow of agent pump 47 is stopped, the radioactivity detectors 43*a* and 43*b* begin measuring (or counting) the radioactivity contained in the transparent part of the flow cell (from time points a) through b)). The radioactivity is measured by detecting the flash of photons generated by the interaction of radiation particles (such as beta particles from carbon-14 isotopes, etc.) with either liquid or solid scintillators by using usually a pair of photomultiplier tubes inside the radioactivity detector. This process is also called counting radioactivity because the measurement process is actually counting the radiation events associated with the decay of radioactive isotopes.

Since the counting time can be controlled by the user, any desired levels of accuracy on the radioactivity counting or measurement can be achieved. The more counts are accumulated or the longer the fraction is counted, the more accurate results one will obtain from the radioactivity detectors 43*a* and 43*b* for the sample. This is due to the nature of the radiation which is a random process and follows the distribution curve of the Poison distribution statistically. The counts accumulated from this entire counting period is calculated as the mean to represent the radioactivity of the fraction F1. The percent error of the counting, together with other parameters, can be calculated as well to indicate the performance of the counting process.

The flushing phase, which is illustrated as being between time points b) and c) in FIG. 2, is beneficial to the accuracy of the measurements because it diminishes or eliminates radioactivity which might be carried over to next fraction. After accumulating the counts for either a predefined period of time (e.g. 2 min) or based on predefined criteria for counting accuracy or counting errors, the time point b) is encountered. The term "time point" as used herein encompasses a chronological point as well a particular point that is reached according to another criteria. In order to remove the residual radioactivity residing inside the flow cell and eliminate any possible cross contamination for the next incoming fraction, the agent pump 47 starts pumping, at a same or different flow rate of liquid scintillation fluid, if a liquid cell is used. If a solid cell is used, pump 47 will be pumping a non-radioactive solvent or solvent mixture. This flushing phase is to remove any residual radioactivity out of the either solid or liquid cells before the introduction of the next fresh fraction (e.g. fraction between time points T1 and T2). If the flushing phase is performed through flushing apparatus 17, the push-in phase could be a optional phase. However, if the push-in phase is not performed, then the flushing phase preferably should be performed through flushing apparatus 17, as distinguished from through tee 35, to avoid any loss of radioactivity residing between mixing tee 35 and flow cell 12.

The completion of the five phase operations complete the stop-flow counting cycle for the first fraction F1 and the counting result is registered at T1 in FIG. 2E. At time point c), the flow and gradient (if any), of the eluate pump 31 is resumed for another counting cycle. When the gradient is resumed, it starts from the point where it was stopped previously. This will enhance the performance in separation and resolution.

After finishing the stop-flow counting cycle for fraction F1, the next cycle continues for the next fraction F2, etc. In FIG. 2, the counting cycles each counts the corresponding fraction (F1 through F5). The results of the counting cycles are shown in the radiochromatogram in FIG. 2E which has five data points, each of which representing the counting results from corresponding fractions (F1 through F5). In this example, a peak is accurately detected in at T4. The time scale on FIG. 2A is the time scale for a continuous run. The time scales in FIG. 2B through FIG. 2D are the actual time scales including the stop-flow counting process. The time scale in FIG. 2E is the reconstructed time scale by eliminating the time spent during the stop-flow counting cycles. However, the reconstructed radiochromatogram does represent the radioactivity distribution of each fractions in FIG. 2A. There was no changes in the chromatographic separation and retention times using the stop-flow counting method comparing to the normal continuous run in the prior art. The sensitivity and accuracy of radioactivity counting is dramatically improved due to the fact that the counting time of each individual fraction of the eluate can be lengthened as long as the user prefers.

Figure 3:
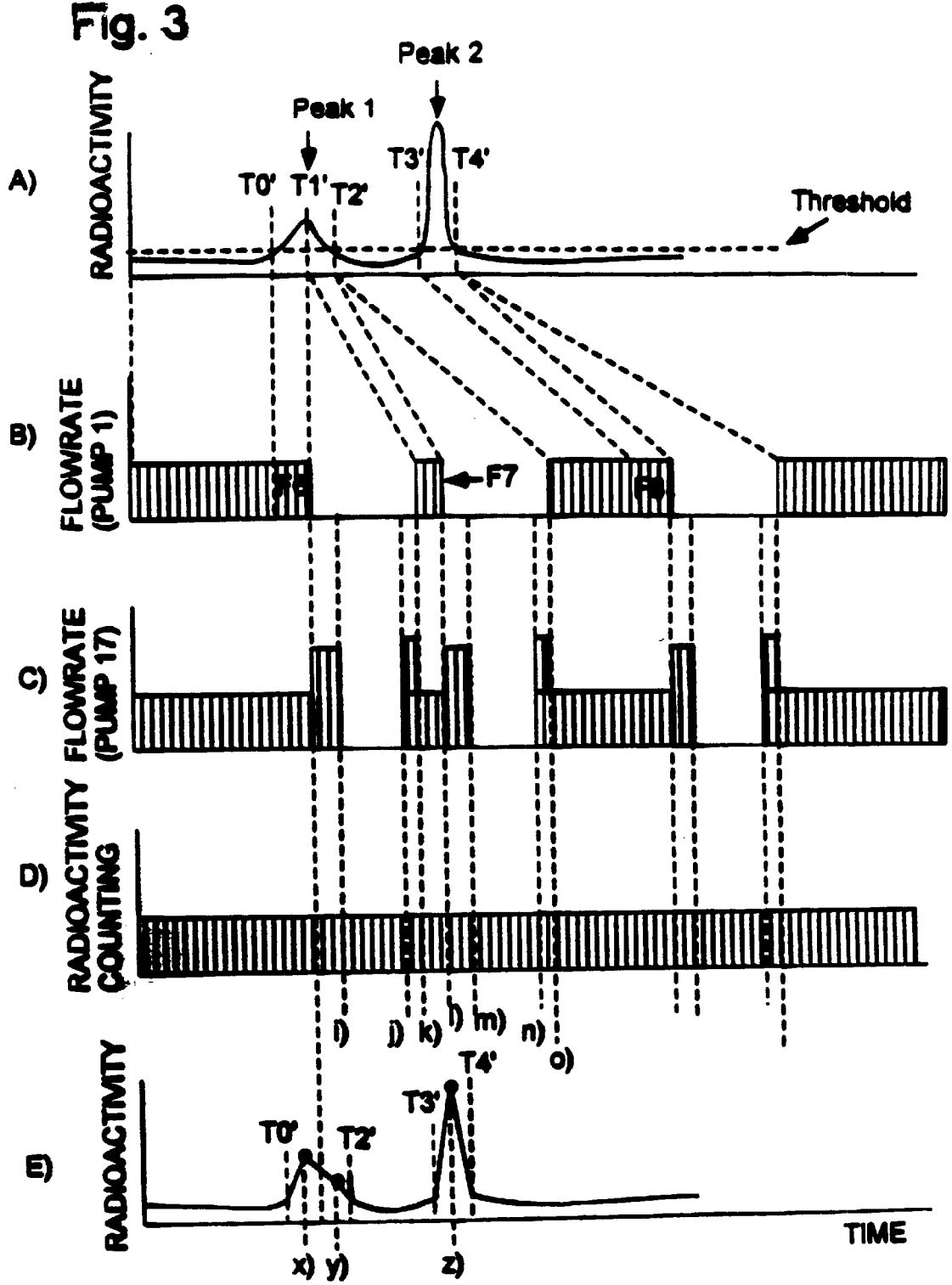
FIGS. 3A through 3E are diagrams illustrating the phases of a method according to an aspect of the present invention employing a second operating mode.

FIG. 3 illustrates the method in which stop-flow counting for radioactive peaks is employed upon exceeding the pre-defined criteria (either by threshold or other algorithms). As an example, a threshold is used to detect the peaks. FIG. 3A shows the radiochromatogram of a sample containing two radioactive peaks if the sample was run under normal method in the prior art (i.e. continuous run with a on-line radioactivity flow-through detector). A threshold in FIG. 3A is preset to recognize any peaks for stop-flow counting. FIG. 3B shows the flowrate of pump 31. Eluate fractions F6, F7, and F8 are subjected to stop-flow counting. FIG. 3C shows the flowrate of pump 47 for delivering liquid scintillation fluid. If a solid cell is used, the pump 47 only delivers the non-radioactive flushing solvent(s) for push-in (from T1' to I) and from l) to m)) and flushing phases (from j) to k)). FIG. 3D shows the counting operation in the radioactivity detectors 43a and 43b. Basically, all the data from the entire run are being used to generate the radiochromatogram as shown in FIG. 3E. The data acquired while the pump 31 stops is calculated as a single data point (as the mean) to represent the corresponding fraction inside the flow cell. FIG. 3E shows the reconstructed radiochromatogram obtained from this counting method.

Using this method, the stop-flow counting cycles are triggered by the radioactive peaks exceeding the pre-defined threshold. Once a peak is detected, the stop-flow counting cycle continues until the end of the radioactive peak is detected (below the threshold).

After the sample is injected, pump 31 starts the flow and gradient (if any). At the same time, pump 47 starts pumping liquid scintillation fluid if a liquid cell is used. If a solid cell is used, pump 47 does not pump anything. When the radioactivity detectors 43a and 43b detect peak 1 at time point T0' (based on either a higher radioactivity than the preset threshold or other algorithms such as changes in slope, etc.), the stop-flow counting cycle starts. The controller 19 stops pump 31 and turns valve 33 to its closed position after the flow phase is finished (from time points T0' to T1'). Pump 47 pumps the fresh scintillant to precisely push-in the eluate or mixture of eluate with scintillant still residing inside the mixing tee 35 and inlet conduit 40 so that the entire fraction is precisely positioned into the flow cell 12. This push-in phase is showed between time points T1' and I). After the push-in phase, the fraction inside the flow cell 12 is counted for a predefined period of time or to accumulate enough counts to reach certain levels of counting accuracy in the static counting phase (from time point I) to time point j)). In this example, fraction F6 containing eluate from time points T0' through T1' is counted first (from time point I) to j)). The accumulated counting data are calculated by as the mean and represent the radioactivity level of the fraction, which is shown as the data point of x) in FIG. 3E. After the static counting phase, the content of the flow cell is flushed out by solvent(s) or scintillant delivered by pump 47 between time points j) and k) through tee 35 of flushing apparatus 17. This completes the five phases of stop-flow counting cycle for fraction F6. At time point k) the flow and gradient (if any) of pump 31 and scintillant flow of pump 47 (if a liquid cell is used) are resumed. The second fraction-fraction F7 is subjected to the counting cycle from time point k) to point n). After the stop-flow counting of the first peak is finished based on predefined threshold, the flow of pump 31 continues until the next peak (peak 2) is encountered. In this example, peak 2 is narrow enough so that one fraction (F8) containing eluate from time point T3' through T4' is needed to count the entire peak. The entire peak 2 is counted in a stationary manner and the obtained data is presented as z) in radioachrmatogram of FIG. 3E. The accumulated counts for each fraction is calculated as the mean to represent the radioactivity of that fraction and positioned at the center position of that fraction on the time axis. In other words, radioactivity data from fraction F6 is positioned at the center of the fraction between T0' and T1' on the time axis and data from fraction F7 is positioned at the center between T1' and T2', etc. The counting data which are obtained by the radioactivity detectors 43a and 43b during the regions where no peaks are detected and counted, will be treated raw data in a conventional manner.

This counting cycle can be applied to all the peaks detected in a LC run. The accurate quantitation of radioactive peaks are thus possible by this stop-flow counting method of present invention. A broad peak may be counted in several consecutive fractions. A sharp or narrow peak may be counted in a single fraction. Since the counting time can be controlled, any desired levels of counting accuracy can be obtained. Furthermore, since the fraction size can be controlled, the desired resolution of radiochromatogram can be achieved for any peaks.

The present method encompasses employing the flow, push, and measuring stages without the flushing stage. Further, in some particular embodiments, the present invention encompasses employing the flow, measuring, and flush stages, without the push stage. Further, for those who have ordinary skills in this field, it is easy to understand that many variations of this method can be used. Based on the same principle, a region or regions of the interest during a LC chromatogram can be measured accurately for the radioactivity. Similarly, when the beginning of the region(s) is reached, the control arrangement will send signals to stop the flow and pause the gradient and the radioactivity detection means 13 starts the counting process in a stationary manner for a period of time. Depending on the width of the regions of interest, each of region can be counted as more than one fraction.

According to another aspect of the method according to the present invention, after a fraction residing in the flow cell has been counted (or otherwise sensed or measured, depending on the particular radioactivity measuring system or process employed) to determine the radioactivity in the fraction, a gas, preferably an inert gas such as helium or nitrogen, may be flowed through flushing tube 110 to remove the contents of the detection tube 105 downstream of the open end 112. Alternatively, in embodiments that do not include the gas purging or flushing system 17, the liquid agent may be employed for flushing. Further, the present invention encompasses employing both the agent and the gas sequentially to perform the flushing operation.

Figure 4:
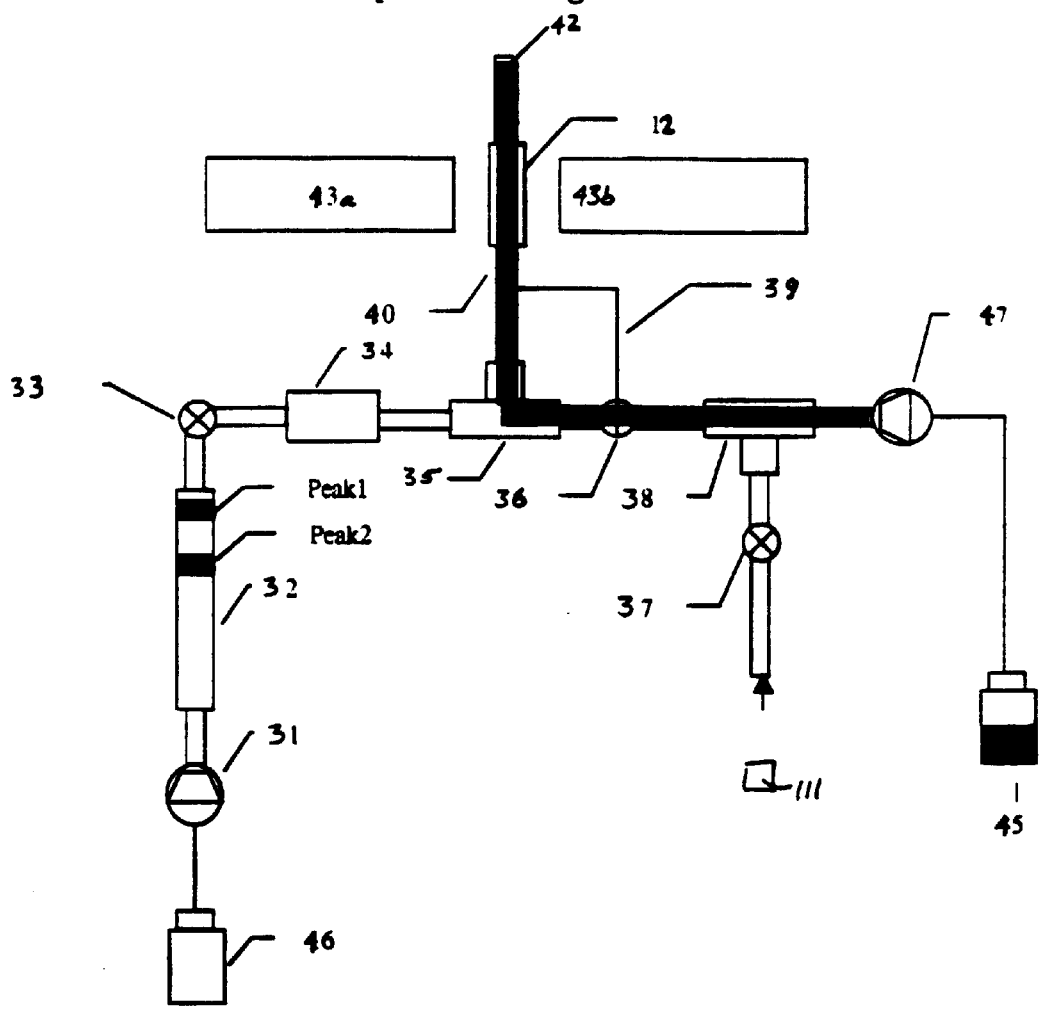
FIG. 4 is a simplified schematic similar to that shown in FIG. 1 illustrating the precise positioning of each eluate fraction.
Figure 5:
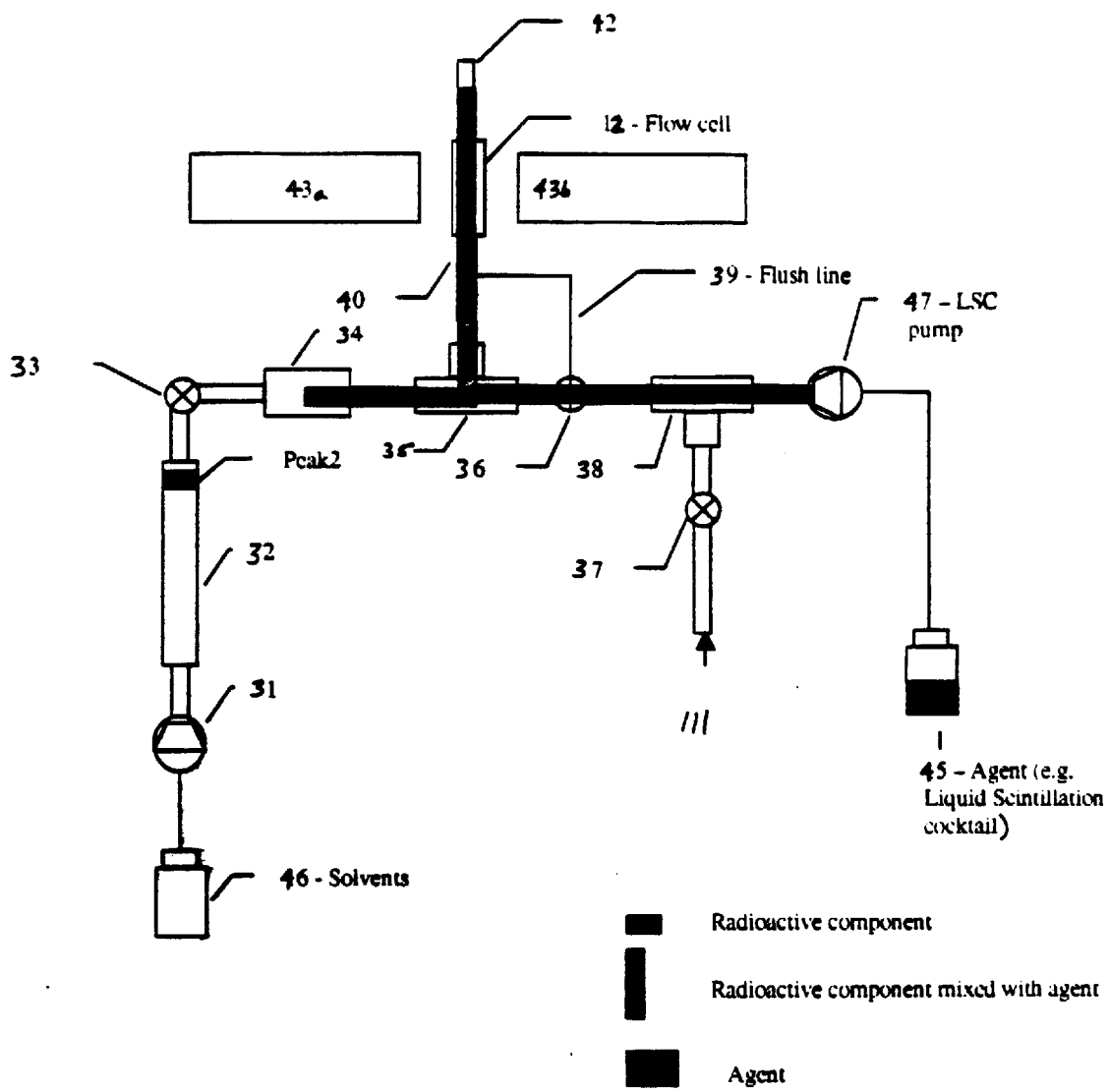
FIG. 5 is a simplified schematic similar to that shown in FIG. 1 illustrating the flow phase in which a fraction is collected in the flow cell.

It will be appreciated that the portion of the sample residing within the detection area of the cell 12 upstream of the open end of the flushing tube (i.e., within the portion of the tube designed by reference numeral 117 in FIG. 4) will not be purged by the gas stream described above, and thus will remain within the tube even after the flushing operation. Preferably, after the aforementioned flushing, further sample will be advanced into detection area of the cell, with the small portion 117 being the leading edge of the new fraction, which is disposed at a distal end portion of tubular means 105 that is exposed to the detectors 43a and 43b. Preferably, the pumps will advance a volume of the sample into the detection area such that the portion of the sample formerly residing in position 117 is at the end of the detection area of the cell 12, or, more preferably, just beyond the end of the detection area of the cell 12. Thus, in preferred embodiments, the eluate formerly residing in position 117 will not be counted twice.

Stop flow detection/quantitation of radioactivity has been reported previously. However, it is hereto not been known to require positioning of the eluate fractions into the effective portion of the flow cell before static counting occurs. A disadvantage of the prior system is that the "dead volume" between the mixing tee and the beginning of the effective transparent portion of the flow cell contains a portion of the radioactive fraction which has not been counted for radioactivity in the flow cell before it could be flushed out if the flushing step is performed using the scintillant or cocktail. Thus, such a system may result in inaccurate counting of radioactive components. In contrast, the present invention provides, in some embodiments, for the precise positioning of fractions into the detection area of the flow cell (i.e., the part of the flow cell from which radioactivity is counted).

As used herein, the term "agent" is intended to mean a liquid that is used for flushing the flow cell after counting to displace radioactive sample, or remove residual radioactivity from the flow cell (i.e., to reduce the "memory effect" of the prior sample), or both. Agents include scintillation cocktails, organic solvents such as methanol, acetonitrile, or mixtures of organic solvents, and detergent solutions. Any of such agents can be used with either liquid or solid cells. However, for liquid cells, i.e., cells in which the scintillant is contained within the sample solution, the agent is preferably scintillation cocktail. For solid cells, i.e., cells in which the detection area of the flow cell is packed with a solid scintillant, solvents are preferred agents.

As used herein, the term "radioactivity" has its accustomed meaning as decay products from unstable isotopic species. The term, "radiolabeled species" means a chemical species that contains a radioactive moiety.

As used herein, the term "eluate from a chromatography column" is intended to mean the outflow from a liquid chromatography column. The liquid chromatography columns contemplated by the present invention include HPLC (high pressure liquid chromatography) columns, including standard size and capillary columns, as well as other liquid chromatography columns operated at lower pressure, which are well known in the art to be useful, for example only, in the separation of organic molecules and biological molecules.

The term "radiation detection area" as applied to flow cells described herein refers to that portion of the flow cell from which radiation can be detected by photomultiplier tubes of the radioactivity detector.

As used herein, the terms "upstream" and "downstream" refer to a direction of the flow within the system. As used herein, the term "remove" as applied to the purging of the liquid from any portion of a flow cell shall be understood to refer to at least substantially complete displacement of said sample.

It is thought that the stop-flow counting apparatus and method of the present invention and many of its attendant advantages will be understood from the foregoing description and it will be apparent that various changes may be made in the form, construction and arrangement of the parts thereof without departing from the spirit and scope of the invention or sacrificing all of its material advantages, the form hereinbefore described being merely a preferred or exemplary embodiment thereof.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for measuring the radioactivity of an eluate from a liquid chromatography column, the method comprising:
    (a) providing a liquid chromatograph comprising:
        (i) a liquid chromatography column;
        (ii) a radioactivity detector comprising a flow cell, said flow cell having a radiation detection area from which radioactivity is counted;
        (iii) a conduit for conducting said eluate from said chromatography column into said flow cell of said radioactivity detector;
        (iv) means for introducing an agent solution into said eluate interposed in said conduit;
    (b) flowing said eluate into said flow cell;
    (c) stopping said flow of said eluate;
    (d) flowing a volume of said agent solution into said conduit that is sufficient to ensure that said eluate residing in said means for introducing said agent solution, in said conduit downstream of said means for introducing said agent solution, and in said flow cell preceding said radiation detecting region is placed into said radiation detection area of said flow cell;
    (e) counting the radioactivity of the solution in said radiation detection area in a static fashion, and
    (f) optionally flushing said flow cell;
    (g) optionally repeating steps (b) through (g).

2. The method of claim 1 wherein said flushing in said step (f) comprises the steps of:
    h) flushing said flow cell with a first fluid;
    i) optionally flushing said flow cell with a second fluid; and
    j) optionally flushing said flow cell with a third fluid;
wherein each of said fluids is independently a gas, a solvent or an agent solution.

3. The method of claim 2 wherein said first fluid and said third fluid are each an inert gas, and said second fluid is a solvent or an agent solution.

4. The method of claim 2 wherein said first fluid and said third fluid are each a solvent or an agent solution, and said second fluid is an inert gas.

5. The method of claim 2 wherein said flushing of said flow cell with gas is performed with a steady stream of gas.

6. The method of claim 2 wherein said gas is nitrogen or helium.

7. The method of claim 2 wherein said flushing of said flow cell with gas is performed with pulses of gas.

8. The method of claim 2 wherein said flow cell is a liquid flow cell.

9. The method of claim 2 wherein said liquid chromatograph further comprises a UV-visible absorbance detector.

10. The method of claim 9 wherein steps b–g are performed only when a threshold amount of UV or visible electromagnetic radiation is detected by said UV-visible absorbance detector.

11. The method of claim 2 wherein steps b–g are performed for every fraction elated from said chromatography column.

12. The method of claim 2 wherein steps b–g are performed only when a threshold amount of radioactivity is detected by said radioactivity detector.

13. The method of claim 1 wherein said step (b) further comprises simultaneously flowing said agent solution to produce a mixed eluate-agent solution in said conduit; and flowing said mixed eluate-agent solution into said flow cell.

14. The method of claim 1 wherein, in step (b), said agent solution is simultaneously flowed into said flow cell with said eluate.

15. The method of claim 14 wherein said flushing in said step (f) comprises the steps of:
   i) flushing said flow cell with a first fluid;
   j) optionally flushing said flow cell with a second fluid; and
   k) optionally flushing said flow cell with a third fluid;
wherein each of said fluids independently a gas, a solvent or an agent solution.

16. The method of claim 15 wherein said first fluid and said third fluid are each an inert gas, and said second fluid is a solvent or an agent solution.

17. The method of claim 15 wherein said first fluid and said third fluid are each a solvent or an agent solution, and said second fluid is an inert gas.

18. The method of claim 15 wherein said flushing of said flow cell with gas is performed with a steady stream of gas.

19. The method of claim 15 wherein said gas is nitrogen or helium.

20. The method of claim 15 wherein said flushing of said flow cell with gas is performed with pulses of gas.

21. The method of claim 15 wherein said flow cell is a liquid flow cell.

22. The method of claim 15 wherein steps b–g are performed for every fraction eluted from said chromatography column.

23. The method of claim 15 wherein steps b–g are performed only when a threshold amount of radioactivity is detected by said radioactivity detector.

24. The method of claim 15 wherein said liquid chromatograph further comprises a UV-visible absorbance detector.

25. The method of claim 24 wherein steps b–g are performed only when a threshold amount of UV or visible electromagnetic radiation is detected by said UV-visible absorbance detector.

26. A method for determining the radioactivity of an eluate from a liquid chromatography column, said method comprising:
   a) providing a liquid chromatograph comprising:
      (i) a liquid chromatography column;
      (ii) pump means for pumping solvent through said chromatography column to produce an eluate;
      (iii) a radioactivity detector comprising a flow cell, said flow cell having a radiation detection area from which radioactivity is counted;
      (iv) a first conduit for introducing said eluate into said flow cell of said radioactivity detector;
      (v) mixing means disposed in said first conduit;
      (vi) a second conduit for introducing an agent solution into said mixing means;
      (vi) pump means for pumping said agent solution; and
      (vii) an optionally present UV-visible absorbance detector;
   b) either:
      (1) pumping said eluate into said radiation detector so that at least part of said radiation detection area of said flow cell is occupied by said eluate; or
      (2) simultaneously pumping said eluate from said chromatography column and said agent solution through said mixing means so that at least part of said radiation detection area of said flow cell is occupied by said mixed eluate-agent solution;
   c) stopping said flow of said eluate or said mixed eluate-agent solution;
   d) pumping a volume of said agent solution through said second conduit and said mixing means and into said first conduit, said volume of agent solution being sufficient to ensure that said eluate or said mixed eluate-agent solution residing in said first conduit, said mixing means and said flow cell preceding said radiation detection area is placed into said radiation detection portion of said flow cell;
   e) counting the radioactivity residing in the radiation detection portion of the flow cell in a static fashion;
   f) flushing at least said radiation detection area of said flow cell with said agent solution; and
   g) optionally repeating steps (b) through (f).

27. The method of claim 26 wherein said second conduit comprises means for the introduction of a gas into said second conduit.

28. The method of claim 27 further comprising the step of flushing at least said radiation detection area of said flow cell with said gas, said gas flushing step being performed either immediately before or immediately after step (f).

29. The method of claim 28 wherein said gas is an inert gas.

30. The method of claim 28 wherein said gas is nitrogen or helium.

31. The method of claim 28 wherein said mixing means disposed in said first conduit is a mixing tee.

32. The method of claim 28 wherein said means for the introduction of a gas into said second conduit is a tee.

33. The method of claim 28 wherein said agent solution comprises a scintillant.

34. The method of claim 28 wherein steps b–f are performed for every fraction eluted from said chromatography column.

35. The method of claim 28 wherein said flushing is performed with a steady stream of gas.

36. The method of claim 28 wherein said flushing is performed with pulses of gas.

37. The method of claim 26 wherein steps b–f are performed for every fraction eluted from said chromatography column.

38. The method of claim 26 wherein steps b–f are performed only when a threshold amount of radioactivity is detected by said radioactivity detector.

39. The method of claim 26 wherein steps b–f are performed only when a threshold amount of UV or visible light is detected by said UV-visible absorbance detector.

40. In a stop-flow method for measuring the radioactivity of a radiolabeled sample solution, the method comprising:
   (a) introducing a sample solution containing at least one radiolabeled species and an agent solution into a means for mixing said sample solution and said agent solution to produce a mixed sample-agent solution;
   (b) flowing said mixed sample-agent solution from said mixing means through a conduit and into a flow cell having a radiation detection area for detection of radioactivity;

(c) stopping said flow of said mixed sample-agent solution; and (d) counting the radioactivity of said mixed sample within said radiation detection area;

the improvement comprising:

after step (c) flowing a volume of said agent solution through said mixing means and into said conduit between said mixing means and said flow cell in an amount at least equal to the volume of said conduit and said mixing means, to ensure that said volume of mixed agent-sample solution residing in said conduit and said mixing means is placed in said radiation detection area prior to counting in step (d).

41. The method of claim 40 wherein said method further comprises the step of:

(e) flushing said flow cell with said agent solution to remove said sample solution from said flow cell.

42. The method of claim 41 wherein said agent solution comprises a scintillant.

43. In a stop-flow method for measuring the radioactivity of a radiolabeled sample solution, the method comprising:

(a) introducing a sample solution containing at least one radiolabeled species through a conduit and into a solid flow cell having a radiation detection area for detection of radioactivity, said conduit having interposed therein means for introducing an agent solution into said conduit;

(b) stopping said flow of said sample solution; and (c) counting the radioactivity of said sample solution within said radiation detection area; the improvement comprising:

after step (b) flowing a volume of an agent solution through said introducing means and into said conduit in an amount at least equal to the volume of said conduit and said introducing means, to ensure that said volume of sample solution residing in said conduit and said introducing means is placed in said radiation detection area prior to counting in step (c).

44. The method of claim 43 wherein said method further comprises the step of:

(d) flushing said flow cell with said agent solution to remove said sample solution from said flow cell.

45. The method of claim 44 wherein said agent solution is a solvent.

46. A method for measuring radioactivity in an eluate from a chromatography column comprising the steps of:

(a) providing a liquid chromatograph comprising:

(i) a liquid chromatography column producing an eluate;

(ii) a radioactivity detector comprising a flow cell, said flow cell having a radiation detection area from which radioactivity is counted;

(iii) means for mixing said eluate and an agent solution to form a mixture thereof;

(iv) conduit means for directing said mixture into said flow cell; and (v) means for introducing a gas into said flow cell; and (vi) an optionally present UV-visible absorbance detector;

(b) flowing said mixture of said eluate and said agent solution through said conduit and into said radiation detection area of said flow cell;

(c) stopping said flow of said mixture;

(d) flowing a volume of said agent solution through said mixing means and into said conduit means in an amount at least equal to the total volume of said conduit, said mixing means and said flow cell preceding said radiation detection area, to ensure that said volume of mixed agent-sample solution residing in said conduit and said mixing means is placed in said radiation detection area;

(e) counting the radioactivity of said mixed sample within said radiation detection area; and (f) flushing at least said radiation detection of said area flow cell with said gas to remove sample mixture therefrom; and (g) optionally repeating steps (b)–(f).

47. The method of claim 46 further comprises the step of:

(h) flushing said flow cell with said agent solution.

48. The method of claim 47 wherein said agent solution is a solution comprising a scintillant.

49. The method of claim 47 wherein said step (g) is performed immediately preceding or immediately after step (f).

50. The method of claim 49 wherein said gas is an inert gas.

51. The method of claim 49 wherein said gas is nitrogen or helium.

52. The method of claim 49 wherein said flow cell is a liquid flow cell.

53. The method of claim 49 wherein steps b–f are performed for every fraction eluted from said chromatography column.

54. The method of claim 49 wherein steps b–f are performed for every fraction eluted from said chromatography column.

55. The method of claim 49 wherein steps b–f are performed only when a threshold amount of radioactivity is detected by said radioactivity detector.

56. The method of claim 49 wherein steps b–f are performed only when a threshold amount of radioactivity is detected by said radioactivity detector.

57. The method of claim 49 wherein steps b–f are performed only when a threshold amount of UV or visible light is detected by said UV-visible absorbance detector.

58. The method of claim 49 wherein steps b–f are performed only when a threshold amount of UV or visible light is detected by said UV-visible absorbance detector.

59. The method of claim 49 wherein said flushing with said gas is performed with a steady stream of said gas.

60. The method of claim 49 wherein said flushing with said gas is performed with a discontinuous stream of said gas.

61. The method of claim 49 wherein said flushing with said gas is performed with pulses of said gas.

62. A method for measuring radioactivity in an eluate from a chromatography column comprising the steps of:

a) providing a liquid chromatograph comprising:

(i) a chromatography column providing an eluate therefrom;

(ii) a radioactivity detector having a flow cell, said flow cell having a radiation detection area from which radiation is counted;

(iii) a conduit for flowing said at least said eluate from said chromatography column into said flow cell, said conduit having disposed means for introducing an agent solution into said conduit and mixing said eluate and an agent solution to form a mixture thereof;

(iv) means for introducing a gas into said flow cell; and (v) a controlable source of said gas;

b) flowing either:
  (i) said mixture of said agent solution and said eluate; or
  (ii) said eluate through said conduit and into said flow cell;
c) stopping said flow of said mixture;
d) flowing a volume of said agent solution through said introducing means and into said conduit means in an amount at least equal to the total volume of said conduit, said introducing means and said flow cell preceding said radiation detecting area, to ensure that said volume of eluate or mixed agent-sample solution residing in said conduit, said introducing means and said flow cell preceding said radiation detecting area is placed in said radiation detection area;
e) counting the radioactivity in said radiation detection area of said flow cell;
f) flushing said flow cell with said gas to remove said eluate therefrom; and
g) optionally repeating steps (b) through (f);
wherein said means for introducing said gas is disposed within said radiation detection area of said flow cell.

63. The method of claim 62 wherein said flow cell comprises:
  i) an exterior surface and an interior surface, said interior surface defining said radiation detection area;
  ii) an inlet through-aperture;
  iii) an exit through-aperture; each of said inlet and exit through-apertures connecting said radiation detection area with said exterior surface;
  iv) tubular means entering through said inlet through-aperture, and exiting through said exit through-aperture, and directing flow of said eluate through said radiation detection area; and
  v) flushing means for flushing the majority of said eluate from said radiation detection area, said flushing means comprising a flushing tube interposed within said tubular means, said flushing means being sealingly connected at one end to a source of gas, and open at the other end; said open end residing inside said tubular means at a point within said radiation detection area of said flow cell; and
  vi) means for entry of said flushing tube into said tubular means.

64. The method of claim 63 wherein said tubular means is in the form of a coil.

65. The method of claim 63 further comprising a grounding wire interposed within said tubular means.

66. The method of claim 65 wherein said grounding wire is in the form of a helix.

67. The method of claim 63 wherein said tubular means is a thermoplastic polymer tube.

68. The method of claim 63 wherein said tubular means is a teflon tube.

69. The method of claim 63 wherein said gas is an inert gas.

70. The method of claim 69 wherein said gas is helium or nitrogen.

71. The method of claim 63 wherein said flow cell is a liquid flow cell.

72. The method of claim 63 wherein said flow cell is a solid flow cell.

73. The method of claim 63 further comprising the step of flushing said flow cell with a fluid.

74. The method of claim 73 wherein said fluid flushing step is performed before of after step (f).

75. The method of claim 63 wherein said means for entry of said flushing tube is located on said tubular means at a point prior to said inlet through-aperture.

76. The method of claim 63 wherein said flow cell further comprises a flushing line through-aperture connecting said exterior surface and said inlet through aperture, said flushing tube being disposed within said flushing line through-aperture, and wherein said means for entry of said flushing tube into said tubular means is located on said tubular means at a point within said inlet through aperture.

77. The method of claim 63 wherein said flow cell further comprises a flushing line through-aperture connecting said exterior surface and said interior surface, said flushing tube being disposed within said flushing line through-aperture, and wherein said means for entry of said flushing tube into said tubular means is located on said tubular means at a point within said radiation detection area.

78. The method of claim 63 wherein said flushing of said flow cell with said gas in step (f) comprises directing a steady stream of gas through said flushing means.

79. The method of claim 63 wherein said flushing of said flow cell with said gas in step (f) comprises directing a discontinuous stream of gas through said flushing means.

80. The method of claim 63 wherein said flushing of said flow cell with said gas in step (f) comprises directing a pulses of gas through said flushing means.

81. The method of claim 63 wherein said liquid chromatograph further comprises a UV-visible absorbance detector.

82. A stop flow method for measuring the radioactivity of a sample in a flow cell comprising the steps of:
  (a) providing a stop flow apparatus comprising a flow cell and conduit means for delivering a liquid sample containing at least one radioactive species to the flow cell, said conduit means including introducing means for introducing a non-sample liquid into the conduit means;
  (b) flowing the liquid sample through the conduit and into the flow cell;
  (c) stopping the flow of the liquid sample; and
  (d) flowing a non-sample fluid through the introducing means and into the conduit means to place the portion of the sample residing in the conduit means after completion of step (c) within the detection area of the flow cell;
  (e) counting the radioactivity of the sample; and
  (d) flowing a volume of gas through the flow cell in an amount sufficient to remove the sample solution from the radiation detection area of the flow cell.

* * * * *